United States Patent [19]

Moniotte

[11] 4,417,012

[45] Nov. 22, 1983

[54] ORGANIC THIOSULPHATES AND THIOSULPHONATES USEFUL AS STABILISING AGENTS FOR RUBBER VULCANISATES

[75] Inventor: Philippe G. Moniotte, Heron, Belgium

[73] Assignee: Monsanto Europe S.A., Brussels, Belgium

[21] Appl. No.: 393,950

[22] Filed: Jun. 30, 1982

[30] Foreign Application Priority Data

Jul. 8, 1981 [GB] United Kingdom ................ 8121098
Aug. 13, 1981 [GB] United Kingdom ................ 8124716

[51] Int. Cl.³ .......................... C08K 5/47; C08K 5/41
[52] U.S. Cl. ............................. 524/83; 260/500.5 R; 260/769; 260/779 R; 260/780; 260/799; 524/94; 524/95; 524/99; 524/102; 524/104; 524/157; 524/159; 524/162; 524/166; 544/4; 544/64; 544/107; 546/2; 546/14; 546/152; 546/186
[58] Field of Search ............... 524/166, 159, 157, 162, 524/83, 94, 95, 99, 102, 104; 260/769, 779 R, 799, 780

[56] References Cited

U.S. PATENT DOCUMENTS

| | | | |
|---|---|---|---|
| 2,936,295 | 5/1960 | Brodkey et al. | 524/166 |
| 3,036,034 | 5/1962 | Rumscheidt | 524/166 |
| 3,535,249 | 10/1970 | Larson | 260/23 |
| 3,732,192 | 5/1973 | Arnold | 260/79.5 B |
| 3,869,435 | 3/1975 | Trivette | 260/79.5 C |

FOREIGN PATENT DOCUMENTS

1388279  3/1975  United Kingdom .

OTHER PUBLICATIONS

Weingarten, F. W., "Taurin-Homologue and Polymethylen-dithioschwefelsaure Salze", Arzneimittel Forschung, 1954, 4, 344–6.
Milligan and Swan, "Cyclic Trisulphides from Bunte Salts", J. Chem. Soc., 1965, 2901–4.
El Hewehi, Z. & Taeger, E., "Notiz über Bunte-Salze", Journal fur Praktische Chemil, 4 Reihe, Band 7, 1958.

*Primary Examiner*—Veronica P. Hoke
*Attorney, Agent, or Firm*—Gordon B. Seward

[57] ABSTRACT

Additives for rubber compositions, giving vulcanisates having improved retention of optimum physical properties, are compounds containing two or more groups of the formula —S—SO$_2$R linked by an organic bridging group, or polymers containing two or more groups of the formula —S—SO$_2$R attached to an organic polymer chain, where R represents (a) a radical OM where M is a monovalent metal, the equivalent of a multivalent metal, a monovalent ion derived by the addition of a proton to a nitrogenous base, or the equivalent of a multivalent ion derived by the addition of two or more protons to a nitrogenous base, or (b) an organic radical selected from aliphatic, cycloaliphatic, aromatic and heterocyclic radicals, and radicals which are combinations of any two or more such radicals.

25 Claims, No Drawings

ORGANIC THIOSULPHATES AND THIOSULPHONATES USEFUL AS STABILISING AGENTS FOR RUBBER VULCANISATES

BACKGROUND OF THE INVENTION

This invention relates to rubber vulcanisates having improved physical properties.

The process of vulcanising diene rubbers by heating with sulphur and a vulcanisation accelerator has been known for many years. By this process vulcanisates having certain physical properties, for instance tensile strength, resilience and fatigue resistance at a high level can be obtained, but such vulcanisates tend not to have good ageing properties. Apart from the addition of antioxidants which will retard oxidative heat ageing, other methods which have been proposed for making vulcanisates having improved ageing properties include the use of lower proportions of sulphur and increased proportions of accelerator relative to those which would be employed for a conventional cure, and the partial or complete replacement of sulphur by other cross-linking agents. Examples of such cross-linking agents include amine disulphides, for example, N,N'-dithiodimorpholine, bis(sulphenamides) as described in GB Pat. No. 1,409,953 and U.S. Pat. No. 3,847,880, and compounds comprising two or more accelerator groupings linked through an organic bridging group as described in GB Pat. No. 1,388,279.

Vulcanisates made using such alternative systems tend, however, to lack certain of the merits of a sulphur-cured vulcanisate. For example, lowering the ratio of sulphur to accelerator or replacing the sulphur partially or completely by an amine disulphide, gives vulcanisates having inferior dynamic properties. The use of the aforementioned bis(sulphenamides) and compounds containing two or more accelerator groupings means that molecular species having accelerator activity as well as those having cross-linking activity are released into the vulcanising system, so that the freedom for variations in compounding, which is possible when the cross-linking agent and the accelerator are added as separate entities, is lost.

BRIEF SUMMARY OF THE INVENTION

According to the present invention we have found that vulcanisates having improved properties can be obtained by adding certain materials in addition to sulphur and a vulcanisation accelerator during the compounding of diene rubbers. These materials have the effect of stabilising the properties of the vulcanisate if the temperature of the vulcanisate unavoidably remains high for a prolonged period after cure, and during the service life of the vulcanisate, and are herein referred to as stabiliser materials.

The invention provides a vulcanisable rubber composition comprising a diene rubber, sulphur and a vulcanisation accelerator, characterised in that the composition also comprises a stabiliser material containing two or more groups of the formula —S—SO$_2$R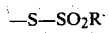

where R represents (a) a radical —OM where M is a monovalent metal, the equivalent of a multivalent metal, a monovalent ion derived by the addition of a proton to a nitrogenous base or the equivalent of a multivalent ion derived by the addition of two or more protons to a nitrogenous base, or (b) an organic radical selected from aliphatic, cycloaliphatic, aromatic and heterocyclic radicals, and radicals which are combinations of any two or more such radicals, the groups of the aforesaid formula being linked by an organic bridging group or attached to an organic polymer chain. The groups are thus thiosulphate groups —S—SO$_2$OM or thiosulphonate groups —S—SO$_2$R in which R is an aforesaid organic radical.

The invention also includes a vulcanisate that has been obtained by heating a vulcanisable rubber composition of the invention at vulcanisation temperature. U.S. Pat. No. 3,535,249 discloses antioxidant compositions for polymers comprising (a) at least one phenolic antioxidant (b) at least one neutralizer that will neutralize the effect of heavy metal ions and (c) at least one reducing agent. In such compositions the reducing agent can be an organic or inorganic thiosulphate, for example sodium benzyl thiosulphate or sodium thiosulphate.

According to U.S. Pat. No. 3,732,192, thiosulphonates of the formula —R—S—SO$_2$R$^1$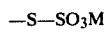 where R and R$^1$ are organic radicals, for instance aryl, alkyl, cycloalkyl radicals and substituted derivatives thereof, are useful in controlling the prevulcanization of vulcanisable diene rubber formulations containing antiozonant and vulcanisation accelerator.

In contrast to this prior art, an essential feature of the stabiliser materials used in the present invention is that they contain at least two thiosulphate or thiosulphonate groups. The type of stabilisation, for example reversion resistance, which is conferred on vulcanisates by the stabiliser materials of the present invention and which is attributable to their di- or poly-functionality, is not shown by the mono—thiosulphates and mono—thiosulphonates of the prior art.

Preferred stabiliser materials are compounds in which the thiosulphate or thiosulphonate groups are each linked to a primary carbon atom of the bridging group, and polymers in which the thiosulphate or thiosulphonate groups are linked to primary carbon atoms in side chains attached to the main polymer chain. The thiosulphate or thiosulphonate groups therefore usually occur in the form —CH$_2$—S—SO$_2$R.

Most materials useful as vulcanisate stabilisers in accordance with the invention are new, and a further aspect of the invention is a material containing two or more groups of the formula

—S—SO$_3$M where M represents a monovalent metal or the equivalent of a multivalent metal, a monovalent ion derived by the addition of a proton to a nitrogenous base, or the equivalent of a multivalent ion derived by the addition of two or more protons to a nitrogenous base, the material being a compound in which the said groups are linked by an organic bridging group, or a polymer in which the said groups are attached to an organic polymer chain; provided that when the material is a compound having the formula MO$_3$S—S—X'—S—SO$_3$M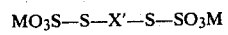

and X' represents a radical —(CH$_2$)$_x$— where x is an integer having a value from 2 to 7 inclusive, 10 or 12, a radical —CH$_2$—CH=CH—CH$_2$—, a radical —CH$_2$COCH$_2$—, a radical —CH$_2$CH$_2$OCH$_2$CH$_2$—, a radical —CH$_2$CH$_2$SO$_2$CH$_2$CH$_2$ or a radical —(CH$_2$)$_n$C$_6$H$_4$(CH$_2$)$_n$— where n has a value from 1 to 3 and C$_6$H$_4$ is para-phenylene, M is not sodium; and provided that when X' represents a radical —(CH$_2$)$_7$— M is not S-benzylisothiouronium.

Stabilisers which are compounds containing groups of the formula —S—SO$_2$R linked by an organic bridging group normally contain two, three or four groups —S—SO$_2$R. Illustrative of such compounds are those having the formula $$X[-(CH_2)_{n'}CH_2-S-SO_2R]_{n''}$$

where n' has an integral value of at least 1, n'' has the value 2, 3 or 4 and X represents the remainder of the bridging group.

In compounds having two groups

—S—SO$_2$R, the bridging group is divalent, and such compounds can be represented by the formula $$RO_2S-S-X'-S-SO_2R$$

In this formula X' can be, for example, a straight- or branched-chain alkylene or alkenylene group, preferably one containing from 2 or from 5 to 40 carbon atoms, and more preferably one containing 5 to 16 carbon atoms. Examples of such groups are ethylene, pentamethylene, hexamethylene, octamethylene, nonamethylene, decamethylene, dodecamethylene, 3-methyl-1,5-pentylene and 1,6-hex-2-enylene. As a variant, a divalent bridging group may be an alkylene or alkenylene group having one or more aryl, for example phenyl, substituents. An example of such a radical is 2-phenyl-1,4-butylene.

In other instances, X' has a structure comprising two or more alkylene units, pairs of such units being linked through an oxygen or sulphur atom, through a group —SO$_2$—, —NH$_2^+$—, —N(C$_{1-6}$alkyl)— or —COO—, or through an arylene or cycloalkylene radical. Representative of such structures are those of the formulae
—(CH$_2$)$_a$—O—(CH$_2$)$_a$—
—(CH$_2$)$_a$—O—CH$_2$—O—(CH$_2$)$_a$—
—(CH$_2$)$_b$—cyclohexylene—(CH$_2$)$_b$—
—(CH$_2$)$_c$—COO—(CH$_2$)$_a$—
—(CH$_2$)$_c$—COO—Y—OOC—(CH$_2$)$_c$—,
each a and each c independently represents an integer of from 2 to 20, each b independently represents an integer of from 1 to 10, and Y represents a group —(CH$_2$)$_c$— or a group —(CH$_2$CH$_2$O)$_d$CH$_2$CH$_2$— where d represents an integer of from 1 to 5. Preferred values for a are from 3 to 8, preferred values for b are 1 to 4, and preferred values for c are from 3 to 18, more especially 3 to 12.

Other examples of the bridging group X' are those having the formula
—(CH$_2$)$_c$—SO$_2$—(CH$_2$)$_c$—
—(CH$_2$)$_c$—NH—(CH$_2$)$_c$— and
—(CH$_2$)$_c$—NH$_2^+$—(CH$_2$)$_c$—
where each c independently has a value from 2 to 20, preferably from 3 to 18, and more preferably from 3 to 12.

Where values of a, b or c exceed 2, the polymethylene groups can be straight chain or branched, but preferably the terminal carbon atom to which the —SO$_2$OR group is attached is a primary carbon atom.

Stabiliser compounds having three or four thiosulphate or thiosulphonate groups include those where three or four groups —C$_m$H$_{2m}$—S—SO$_2$R, m typically having a value from 3 to 6, are substituents in an aromatic nucleus, for example a benzene or naphthalene nucleus, (which may also contain other substituents), or as substituents in one or more nuclei of a di- or trinuclear aromatic compound, for example biphenyl, diphenyl ether, diphenyl sulphone or benzophenone.

Further examples of trivalent bridging groups are those of the formulae
—A$^1$—OCH$_2$CH(OA$^1$—)CH$_2$OA$^1$— and
A—C(A OOCA$^1$—)$_3$
where each A$^1$ is independently an alkylene group, for example a C$_{2-18}$, preferably a C$_{3-12}$, alkylene group and A is C$_{1-6}$alkyl; and also those of the formulae $$N[(CH_2)_c]_3 \text{ and } HN^+[(CH_2)_c]_3$$

where each c independently has a value from 2 to 20, preferably from 3 to 18, more especially from 3 to 12.

Further examples of tetravalent bridging groups are those having the formulae $$C(A^1)_4, Si(A^1)_4 \text{ and } (A^1)_3Si-O-Si(A^1)_3$$

where A$^1$ has the same meaning as before; and those having the formula $$C[CH_2OCO(CH_2)_c]_4$$

where each c independently has a value from 2 to 20, preferably from 3 to 18 and more preferably from 3 to 12.

Examples of polymers are those of the formulae $$\begin{array}{c} CH_2-S-SO_2R \\ | \\ +O-CH_2CH)_{\overline{n'}} \end{array}$$

and esterified and partially esterified polyvinyl alcohols wherein the polymer chain is formed from units selected from —CH—CH$_2$, —CH—CH$_2$—, and —CH—CH$_2$—
   |                  |                        |
   OH                 O                        O
                      |                        |
                      CO                       CO
                      |                        |
                      R'                       (CH$_2$)$_c$
                                               |
                                               S—SO$_2$R where R' represents a C$_{1-12}$-alkyl group and c has an integral value of from 2 to 20, and at least 10%, preferably at least 20%, for example from 25% to 75%, of the units in the polymer are those containing the group —S—SO$_2$R.

The optimum number of carbon atoms in the alkylene units to which the thiosulphate or thiosulphonate groups are attached to bridging groups of the kind described above where two or more alkylene units are linked through atoms or groups, or where the thiosulphate or thiosulphonate groups are attached to units pendant from polymer chains, the optimum value of m in the formula —C$_m$H$_{2m}$—S—SO$_2$R, and the optimum number of carbon atoms in the groups A$^1$, depend on the remainder of the structure of the bridging group. It appears that for a compound to act as an effective stabiliser, the ability to take up certain molecular configurations, i.e. a certain degree of flexibility, is required.

A further requirement is that the relative locations of the thiosulphate or thiosulphonate groups should not be such that significant intramolecular cyclisation can occur when a rubber composition containing the stabiliser material is heated. For example, compounds in which the bridging group is trimethylene or tetramethylene show little stabiliser activity, and it is believed that this is due to the tendency of such compounds to cyclise.

Thus within the class of compounds defined above there will be found differing degrees of stabiliser activity, but methods of evaluation as subsequently described are conventional, and it is therefore a matter of simple and minimum experimentation for the person skilled in the art to determine whether a particular compound will usefully stabilise rubber compositions.

When M in the above formula of the stabiliser material represents a monovalent metal, this can be for instance an alkali metal, for example sodium, lithium or potassium. Sodium is the preferred alkali metal. M can alternatively represent the equivalent of a multivalent metal, for instance magnesium, calcium, barium, zinc, nickel, cobalt or aluminum.

Where M represents a monovalent ion formed by the addition of a proton to a nitrogenous base, the nitrogenous base can be ammonia or a simple primary, secondary or tertiary amine $R^2NH_2, R^2R^3NH$ or $R^2R^3R^4N$ where each of $R^2$, $R^3$ and $R^4$ independently represents an alkyl group, for example a $C_{1-20}$ alkyl group, a $C_{5-9}$ cycloalkyl or alkylcycloalkyl group, for example cyclohexyl or methylcyclohexyl, a benzyl group, a phenyl group or a substituted phenyl group, for example a tolyl or chlorophenyl group, provided that not more than one of $R^2$, $R^3$ and $R^4$ is a phenyl or substituted phenyl group.

Preferred amines are those that are relatively weakly basic. These include amines where weak basicity is a result of steric hindrance around the nitrogen atom due, for example, to the presence of a tert-alkyl group, for instance a tert-alkyl group having from 4 to 12 carbon atoms, such as tert-butyl, tert-amyl or 1,1,3,3-tetramethylbutyl. Examples of such amines are the secondary amines $R^2R^3NH$ where one of $R^2$ and $R^3$ is a tert-alkyl group and the other is a benzyl group or a cyclohexyl or alkylcyclohexyl group. Alternatively both $R^2$ and $R^3$ can be tert-alkyl groups. Further examples are tertiary amines where $R^2$ is a tert alkyl group and $R^3$ and $R^4$ are benzyl groups.

Other suitable weakly basic amines are the primary amines $R^2NH_2$ where $R^2$ is a phenyl or substituted phenyl group, and the secondary amines $R^2R^3NH$ where $R^2$ is a phenyl or substituted phenyl group and $R^3$ is a $C_{1-20}$ alkyl group, preferably a $C_{1-12}$ alkyl group. Examples of such amines are aniline, the toluidines, N-methylaniline, N-butylaniline and N-isohexylaniline. A special class of such secondary amines comprises those where $R^2$ represents a secondary alkyl group, preferably a $C_{3-12}$ secondary alkyl group, or a cyclohexyl group, and $R^3$ represents a 4-phenylaminophenyl group. These amines include compounds such as N-isopropyl-N'-phenyl-p-phenylenediamine, N-sec-butyl-N'-phenyl-p-phenylenediamine, N-1,3-dimethylbutyl-N'-phenyl-p-phenylenediamine, N-1,4-dimethylpentyl-N'-phenyl-p'phenylenediamine and N-cyclohexyl-N'-phenyl-p-phenylenediamine. Such amines function as mono-acid bases despite the presence of the second nitrogen atom in the 4-phenylaminophenyl group, because this second nitrogen atom has virtually no basicity.

Other examples of nitrogenous bases which form thiosulphate salts of the invention are guanidine and substituted guanidines, for example those of the formula

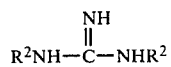

and substituted isothioureas, for example those of the formula

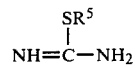

where each $R^2$ independently represents hydrogen, an alkyl group, for example a $C_{1-20}$ alkyl group, a $C_{5-9}$ cycloalkyl or alkylcycloalkyl group, a benzyl group, a phenyl group or a substituted phenyl group; for instance a tolyl group, and $R^5$ represents a $C_{1-20}$ alkyl group, a $C_{5-9}$ cycloalkyl or alkylcycloalkyl group or a benzyl group. Specific examples of substituted guanidines are diphenylguanidine and di-o-tolylguanidine; specific examples of substituted isothioureas are S-ethylisothiourea and S-benzylisothiourea.

Where M represents an equivalent of a multivalent cation formed by the addition of two or more protons to a nitrogenous base, the bases from which such ions can be derived include alkylene diamines, N,N'-disubstituted alkylene diamines, phenylenediamines and N,N'-disubstituted phenylenediamines of the formula

where A represents an alkylene radical $-(CH_2)_c-$ where c has a value of from 2 to 20, preferably from 2 to 12,
and which may be straight chain or branched, or a phenylene, for example a meta- or para-phenylene radical, and each $R^2$ independently represents an alkyl group, for example a $C_{1-20}$ alkyl group, a $C_{5-9}$ cycloalkyl or alkylcycloalkyl group, a benzyl group, a phenyl group or substituted phenyl group, provided that neither $R^2$ is a phenyl or substituted phenyl group when A is a phenylene radical.

In preferred amines where A represents an alkylene radical, $R^2$ is a tert-alkyl group, for example tert-butyl, t-amyl or 1,1,3,3-tetramethylbutyl, or a phenyl group. Examples of such amines are N,N'-diphenylethylene diamine, N,N'-di-tert-butyl-1,4-tetramethylene diamine and N,N'-bis(1,1,3,3-tetramethylbutyl)-1,6-hexamethylene diamine.

In preferred amines where A represents a phenylene radical, $R^2$ is a secondary alkyl group, preferably a $C_{3-12}$ secondary alkyl group or a cyclohexyl group. Examples of such amines are N,N'-di-sec-butyl-p-phenylenediamine, N,N'-bis(1,3-dimethylbutyl)-p-phenylenediamine, N,N'-bis(1,4-dimethylpentyl)-p-phenylenediamine, N,N'-bis(1-ethyl-3-methylpentyl)-p-phenylenediamine, N,N'-bis(1-methylheptyl)-p-phenylenediamine and N,N'-dicyclohexyl-p-phenylenediamine.

Possible bases also include polyalkylene polyamines of the formula $R^2NH-(A'-NH)_n-A'NHR^2$ where A' represents an alkylene radical of from 2 to 8 carbon atoms, n has a value of from 1 to 5, and each $R^2$ independently represents a $C_{1-20}$ alkyl group, a $C_{5-9}$ cycloalkyl or alkylcycloalkyl group, a benzyl group, a phenyl group or a substituted phenyl group.

In other instances, the nitrogen of the nitrogenous base is part of a heterocyclic ring. The base can be monocyclic, for example pyridine, or a compound in which the nitrogen-containing heterocyclic ring is fused to another ring, as for example quinoline. Moreover, the heterocyclic ring can be saturated, as for example in morpholine or piperidine, or it may contain one or more double bonds, as for example in pyrroline or 1,2-dihydroquinoline.

Of the compounds where M represents such a base, those preferred for use as vulcanisate stabilisers are compounds where M represents a 1,2-dihydroquinolinium ion, which may optionally have ring substituents. Examples of such ions are 2,2,4-trimethyl-1,2-dihydroquinolinium, 2,2,4-trimethyl-6-($C_{1-12}$alkoxy)-1,2-dihydroquinolinium, for instance 2,2,4-trimethyl-6-ethoxy-1,2-dihydroquinolinium, 2,2,4-trimethyl-6-($C_{1-18}$alkyl)-1,2-dihydroquinolinium, for instance 2,2,4-trimethyl-6-dodecyl-1,2-dihydroquinolinium, and 2,4-diethyl-2-methyl-1,2-dihydroquinolinium.

Other classes of bases which form divalent cations by the addition of two protons are represented by the general formulae

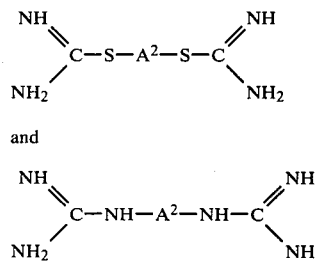

and where $A^2$ represents a radical $-(CH_2)_c-$, where c is an integer from 2 to 20, preferably from 3 to 12, and the radical $-(CH_2)_c-$ can be either straight chain or branched or a $C_{2-20}$ alkenylene or alkadienylene radical, for example a but-2-enylene or octa-2,6-dienylene radical. These bases form bis(isothiouronium) and bis(guanidinium) ions respectively. When R in the groups $S-SO_2R$ of the stabiliser compound is an organic radical, aliphatic radicals from which R may be selected include straight- and branched-chain alkyl and alkenyl groups, more especially such groups containing from 1 to 20 carbon atoms, for example, methyl, ethyl, n-propyl, isopropyl, sec-butyl, tert-butyl, isoamyl, t-amyl, n-hexyl, hex-3-enyl, n-heptyl, n-octyl, 2-ethylhexyl, and decyl, dodecyl, pentadecyl and octadecyl groups.

When R is cycloaliphatic, it is usually a radical containing from 5 to 8 ring carbon atoms, which may be saturated or contain one or two olefinic bonds, for example a cyclopentyl, cyclohexyl or cyclohexenyl group.

An aromatic radical R may be, for example, phenyl, naphthyl or biphenyl, and a heterocyclic radical may be, for example, pyridyl, imidazol-2-yl or thiazol-2-yl.

Radicals which are combinations of two or more of the foregoing radicals include alkylcycloalkyl radicals, for example methylcyclohexyl; alkylaryl radicals, for example tolyl, dimethylphenyl and ethylphenyl; aryla-kyl radicals, for example benzyl and phenethyl; and fused-ring aromatic-heterocyclic radicals, for example quinolyl, benzimidazol-2-yl and benzothiazol-2-yl.

Also included are radicals having substituent atoms or groups, for example halogen such as chlorine or bromine, or nitro, hydroxyl, carboxy, carboalkoxyl or alkylcarbonyl groups. Examples include chloroethyl, chlorotolyl, hydroxyphenyl, carboxypyridyl and nitrobenzothiazolyl.

The stabiliser materials of the invention that are alkali metal salts can be prepared by the nucleophilic substitution of halogen, usually chlorine or bromine, in an appropriate starting material having at least two replaceable halogen atoms, by reaction with an alkali metal thiosulphate. For economic reasons, sodium thiosulphate is preferred, but other alkali metal thiosulphates, for example lithium, potassium or rubidium thiosulphates can be used. For stabiliser compounds having two thiosulphate groups, the reaction can be illustrated by:

$X(Hal)_2 + 2Na_2S_2O_3 \longrightarrow$ $NaOSO_2-S-X-S-SO_2ONa + 2NaHal$ where Hal indicates halogen.

In prior art examples of this type of process, the reaction is usually performed in water or in an aqueous alcoholic medium under reflux (see, for example B. Mulligan and J. M. Swan, Rev. Pure and Applied Chemistry, 1962, 12, 72: and J. Chem. Soc. 1965, 2901).

This reaction tends to be slow, particularly when the halogen to be displaced is chlorine, and we have found it advantageous to use reaction temperatures above the reflux temperatures of aqueous ethanol or methanol mixtures at normal pressures, by carrying out the reaction in an autoclave. For example, the reaction can be carried out at a temperature within the range 100° to 150° C., a preferred range being from 120° to 140° C. At these temperatures, the reaction is usually substantially complete in a short time, for example from 5 to 20 minutes, but longer reaction times can be employed if necessary. We have found it advantageous to add a small amount of sodium sulphite (typically 0.05 to 0.2 mol per mol of sodium thiosulphate) to the reaction mixture. This has the effect of suppressing by-product formation. For solubility reasons, aqueous ethanol or aqueous methanol is generally a more suitable reaction medium than the alcohol alone. The alkali metal thiosulphates, in particular sodium thiosulphate, have sufficient solubility in ethylene glycol and diethylene glycol alone for these glycols to function as satisfactory reaction media. These glycols are therefore the preferred reaction media where the halogen-containing starting material contains hydrolysable groupings. Water introduced with the thiosulphate reactant, if this contains water of crystallisation, e.g. $Na_2S_2O_3 5H_2O$, can be removed by distillation prior to adding the halide reactant. When using ethylene glycol or diethylene glycol, moreover, it is not necessary to operate under pressure in order to achieve reaction temperatures over 100° C.

The quantity of glycol used in the reaction medium should dissolve at least part of the alkali metal thiosulphate, but large amounts of glycol in excess of that required to effect solution are preferably avoided. The glycol (or a mixture of glycols) is preferably essentially the sole component of the reaction medium, although other compatible organic solvents need not be excluded provided the glycol mixture remains the major component of the reaction medium.

Reaction times vary with the reaction temperature and the ease of replacement of the halogen atom or atoms. Typical reaction times for the replacement of chlorine at temperatures within the range 100°–150° C. are from 60 to 15 minutes.

The alkali metal halide by-product in the process of the invention is insoluble in the reaction medium, and precipitates as the reaction proceeds. It can be removed by filtration of the reaction mixture when the reaction is complete. The filtrate is a solution of the organic thiosulphate alkali metal salt from which the organic thiosulphate alkali metal salt can be precipitated by mixing with a solvent which is miscible with the glycol, but is essentially a non-solvent for the alkali metal salt. An example of such a solvent is isopropanol.

Alkali metal salts of organic thiosulphates prepared and isolated in this manner may contain glycol relatively firmly bound in the crystal. So far as the use of the thiosulphate as a rubber stabiliser is concerned, the presence of small amounts of glycol has no adverse effect, but if desired, the glycol can be removed by recrystallisation from a non-glycol solvent.

Stabilisers of the invention where M represents potassium can be made by using potassium thiosulphate as the halogen-displacing reactant in a reaction as discussed above. For the preparation of compounds having other values of M, however, it is in many instances most convenient to prepare the sodium salt as an intermediate from which the sodium is then displaced by the required other cation.

Where the required product is water-soluble, such a displacement can be effected using a cation-exchange resin which carries the required other cation. For example, introduction of a solution of the sodium salt of the organic thiosulphate into a column of cation-exchange resin in which the exchangeable ions are nickel produces as a percolate a solution of the nickel salt of the organic thiosulphate. By essentially the same method, using a cation-exchange resin carrying the cations required in the product, magnesium, calcium, zinc, cobalt and guanidinium salts of the organic thiosulphates can be prepared. The salts in solid form, often containing water of crystallisation, can be obtained by evaporation of the percolates.

The barium salts of the organic thiosulphates are less soluble in water than the alkali metal and certain other metal salts, and crystallise on cooling a solution obtained by mixing hot, concentrated solutions of barium chloride and the organic thiosulphate sodium salt. The barium salts are useful as intermediates in the preparation of other metal salts by double decomposition. Addition of an aqueous solution of the sulphate of the other metal to an aqueous solution of the barium salt (which can be obtained using a sufficient volume of water) results in the precipitation of barium sulphate. This is removed by filtration, giving a filtrate which on evaporation yields the desired metal salt of the organic thiosulphates. Ammonium and certain substituted ammonium salts can also be prepared by this procedure.

Double decomposition procedures using as reactants the alkali metal salts, especially the sodium salts, of the organic thiosulphates and the salts of nitrogenous bases with strong mineral acids, for example hydrochlorides, hydrobromides or sulphates, can be used to prepare stabiliser materials of the invention where M represents a monovalent ion formed by the addition of a proton, or the equivalent of a multivalent ion formed by the addition of two or more protons, to an organic nitrogenous base. The by-product is an alkali metal salt of a strong mineral acid, for example sodium chloride or sodium sulphate, and its separation from the required product is usually straightforward by virtue of their differing solubilities in selected solvents. For instance, the sodium salts of the organic thiosulphates dissolve to a limited extent in warm methanol, as do the sulphates of certain amines, whereas sodium sulphate is virtually insoluble in methanol. On mixing a warm methanolic solution of a sodium salt of an organic thiosulphate with a warm methanolic solution of an amine sulphate, sodium sulphate is precipitated, and can be separated by filtration from the amine salt of the organic thiosulphate which remains in solution. The amine salt itself can be obtained by evaporation of the solvent from the filtrate. This method can be used to prepare salts of amines $R^2R^3NH$ where $R^2$ represents a secondary alkyl group or a cyclohexyl group, and $R^3$ represents a 4-phenylamino group, as well as salts where the cation is an optionally-substituted 1,2-dihydroquinolinium ion.

In other instances, the amine salt of the organic thiosulphate is relatively insoluble in water or aqueous alcohol, and crystallises from the solution obtained by mixing an aqueous or aqueous alcoholic solution of the amine hydrochloride with an aqueous solution of the sodium salt of the organic thiosulphate. N-tert-alkyl-N-benzyl-ammonium, diphenylguanidinium and certain isothiouronium salts can be prepared by this method.

Stabiliser compounds where R in the grouping —S—SO$_2$R represents an organic group can be prepared by the nucleophilic substitution of halogen, usually chlorine or bromine, in an appropriate starting material having at least two replaceable halogen atoms. The reaction can be illustrated, for a compound having two replaceable halogen atoms, by the equation $$2\ RSO_2SM^2 + X(hal)_2 \longrightarrow$$

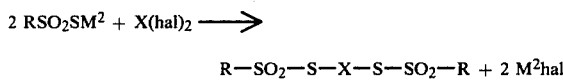

$$R-SO_2-S-X-S-SO_2-R + 2\ M^2hal$$

where R is as defined previously, $M^2$ represents a displaceable ion, usually an alkali metal ion, and hal indicates halogen. Reactions of this type are described in, for example, U.S. Pat. No. 3,047,393 which discloses the reaction of sodium p-toluenethiosulphonate with compounds of the formula $BrX^1Br$ where $X^1$ is a $C_{2-10}$alkylene group, to give compounds of the formula $R^2SO_2SX^1SSO_2R^2$ where $R^2$ is the p-tolyl group.

As an alternative, the general method:

$$2\ RSO_2CL < HS-X-SH \xrightarrow{base}$$

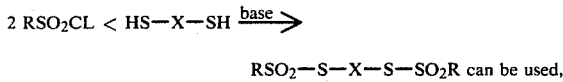

$RSO_2-S-X-S-SO_2R$ can be used,

R being as first defined above to include entities OM.

Specific compounds or classes of compounds useful as vulcanisate stabilisers in the present invention include the salts of
pentamethylene bis thiosulphate
hexamethylene bis thiosulphate
heptamethylene bis thiosulphate
octamethylene bis thiosulphate nonamethylene bis thiosulphate
decamethylene bis thiosulphate
dodecamethylene bis thiosulphate and
hexadecamethylene bis thiosulphate;
with the cations sodium, magnesium, calcium, barium, zinc, cobalt and nickel; with the cations ammonium, $N(C_{4-12}\text{tert-alkyl})$-N-benzylammonium, for example N-tert-butyl-N'-benzylammonium and N-(1,1,3,3-tetramethylbutyl)-N-benzylammonium, N-isopropyl-N-(4-phenylaminophenyl)ammonium, N-(1,3-dimethylbutyl)-N-(4-phenylaminophenyl)ammonium, N-cyclohexyl-N-(4-phenylaminophenyl)ammonium, 2,2,4-trimethyl-1,2-dihydroquinolinium, 6-ethoxy-2,2,4-trimethyl-1,2-dihydroquinolinium, guanidinium and benzylisothiouronium; with divalent cations of the formula $$\overset{+}{R^2NH_2}-A-\overset{+}{NH_2R^2}$$

where A represents para-phenylene and $R^2$ is a $C_{3-12}$ secondary alkyl group, for example a 1,4-dimethylpentyl group;
and with divalent cations of the formula $$[(NH_2)_2CS(CH_2)_cSC(NH_2)_2]^{++}$$

where c has any one of the integral values from 2 to 12 so that $(CH_2)_c$ represents for example tetramethylene, pentamethylene, hexamethylene, octamethylene or decamethylene.

Other classes of compounds useful as vulcanisate stabilisers in the present invention are the compounds $$O[(CH_2)_{a'}S_2O_3Na]_2$$

where a' has any one of the values 3,4,5 and 6, and the compound

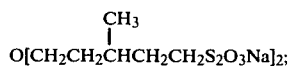

the compounds
$CH_2[O(CH_2)_{a'}S_2O_3Na]_2$ where a' has any one of the values 3, 4, 5 and 6, the compounds
$C_6H_{10}[(CH_2)_{b'}S_2O_3Na]_2$ where b' has any one of the values 1, 2, 3 or 4, and $C_6H_{10}$ is cyclohexylmethylene, the compounds
$NaO_3S_2(CH_2)_{c'}COO(CH_2)_{a'}S_2O_3Na$ where c' has any one of the integral values from 3 to 10 in combination with any one of the values 3, 4, 5 and 6 for a';
the compounds
$NaO_3S_2(CH_2)_{c'}COO(CH_2)_{c''}OOC(CH_2)_{c'}S_2O_3Na$
where each c' has any one of the integral values from 3 to 10 in combination with any one of the integral values from 2 to 12 for c''; the compounds
$NaO_3S_2(CH_2)_{c'}COO(CH_2CH_2O)_{d'}CH_2CH_2OOC(CH_2)_{c'}S_2O_3Na$ where each c' has any one of the integral values from 3 to 10 in combination with any one of the values 1, 2 and 3 for d';
and the corresponding potassium, magnesium, calcium, barium, zinc, nickel and cobalt salts; The compounds $O[(CH_2)_{a'}S_2O_3M]_2$ where a' has any one of the values 3, 4, 5 and 6, and the compounds $$MO_3S_2(CH_2)_{c'}COO(CH_2)_{a'}S_2O_3M$$

where c' has any one of the integral values from 3 to 10 in combination with any one of the values 3, 4, 5 and 6 for a' and where in each case M is selected from cations $N(C_{4-12}\text{tert-alkyl})$-N-benzylammonium, for example N-tert-butyl-N-benzylammonium and N-(1,1,3,3-tetramethylbutyl)-N-benzylammonium, N-isopropyl-N-(4-phenylaminophenyl)ammonium, N-(1,3-dimethylbutyl)-N-(4-phenylaminophenyl)ammonium, N-cyclohexyl-N-(4-phenylaminophenyl)ammonium, 2,2,4-trimethyl-1,2-dihydroquinolinium, 6-ethoxy-2,2,4-trimethyl-1,2-dihydroquinolinium, guanidinium and benzylisothiouronium; and equivalents of divalent cations $$\overset{+}{R^2NH_2}-A-\overset{+}{NH_2R^2}$$

where A represents para-phenylene and $R^2$ is a $C_{3-12}$ secondary alkyl group, for example a 1,4-dimethylpentyl group; and divalent cations $$[(NH_2)_2CS(CH_2)_cSC(NH_2)_2]^{++}$$

where c has any one of the integral values from 2 to 12, the compounds $$NaO_3S_2\!\!-\!\!(CH_2)_4O\!\!-\!\!_m\!(CH_2)_4S_2O_3Na$$
$$m = 1-10$$
$$CH_3N[(CH_2)_3S_2O_3Na]_2$$

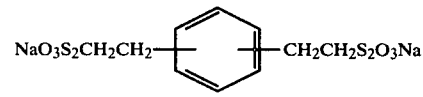

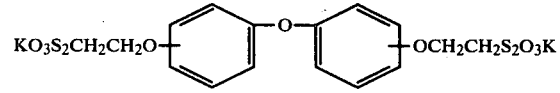

Pentamethylene bis(phenylthiosulphonate)
Hexamethylene bis(phenylthiosulphonate)
Octamethylene bis(o-tolylthiosulphonate)
Decamethylene bis(p-tolylthiosulphate)
Decamethylene bis(methylthiosulphonate)
Decamethylene bis(p-chlorophenylthiosulphonate), compounds having the formula $$MO_3S_2\!-\!(CH_2)_c\!-\!SO_2\!-\!(CH_2)_cS_2O_3M$$

where M represents sodium or the two M's together represent zinc, nickel or cobalt and each c has an integral value from 3 to 12,
and compounds having the formula $$MO_3S_2\!-\!(CH_2)_c\!-\!NH\!-\!(CH_2)_c\!-\!S_2O_3M$$

or $$[MO_3S_2\!-\!(CH_2)_c\!-\!NH_2\!-\!(CH_2)_c\!-\!S_2O_3M]^+Hal^-$$

where M represents sodium or the two M's together represent zinc, nickel or cobalt, each c has an integral value from 3 to 12 and $Hal^-$ represents a halide, for example a chloride or bromide, ion.

The stabiliser materials referred to above are especially effective in compositions in which the rubber is cis-polyisoprene, either natural or synthetic, and in blends containing at least 25% by weight of cis-polyisoprene with other rubbers. Preferably the rubber, if a blend, contains at least 40% and more preferably at least 60% by weight of cis-polyisoprene. Examples of other rubbers which may be blended with cis-polyisoprene include poly-1,3-butadiene, copolymers of 1,3-butadiene with other monomers, for example styrene, acrylonitrile, isobutylene and methyl methacrylate, and ethylenepropylene-diene terpolymers.

The amount of stabiliser compound employed in the compositions of the present invention is usually from 1 to 5, for example from 1.5 to 5, parts by weight, and preferably from 2 to 4 parts by weight per 100 parts by weight of rubber.

In the composition of the invention the essential vulcanising agent is sulphur, but other vulcanising agents such as amine disulphides need not be excluded. The amount of sulphur in the compositions is typically from 2 to 3 parts by weight per 100 parts by weight of rubber, but lesser or larger amounts, for example from 1 to 5 parts on the same basis, may be employed.

In the composition of the invention a single accelerator or a mixture of accelerators can be employed. These include thiazole-based accelerators, for example 2-mercaptobenzothiazole, bis(2-benzothiazolyl) disulphide, benzothiazole-2-sulphenamides for instance N-isopropylbenzothiazole-2-sulphenamide, N-tert-butylbenzothiazole-2-sulphenamide, N-cyclohexylbenzothiazole-2-sulphenamide, N,N-diisopropyl-benzothiazole-2-sulphenamide, N,N-dicyclohexyl-benzothiazole-2-sulphenamide and 2(morpholinothio) benzothiazole, thiocarbamylsulphenamides, for example N,N-dimethyl-N',N'-dicyclohexylthiocarbamylsulphenamide and N (morpholinothiocarbonylthio) morpholine. Mixtures of thiazole-based accelerators with diphenylguanidine can be used. Preferred accelerators are the benzothiazole-2-sulphenamides. In the compositions of the invention, these are usually used in amounts of from 0.5 to 1.5 part by weight per 100 parts by weight of rubber.

The vulcanisate stabilisers used in this invention can be incorporated into rubber by conventional mixing procedures, for example by adding them in a Banbury mixer or by adding them to the rubber on a mill. Ordinarily, with liquid or low melting solid vulcanisate stabilisers, no special precautions are necessary for obtaining good dispersions. However, when using higher melting vulcanisate stabilisers it is recommended that they be ground to a fine powder, preferably 70 micrometer particle size or less to ensure adequate dispersion. Such powders may be treated to suppress dust, for example by the addition of oil, or they can be mixed with a binder, for example a polymer latex, and formed into granules or pellets containing up to 5% by weight of binder. They can also be formulated as predispersions in certain rubbery polymers, such as EPDM or ethylene-vinyl acetate rubber, which predispersions may contain, for example, from 15 to 50% by weight of polymer.

The rubber stocks may include reinforcing carbon blacks, pigments such as titanium dioxide and silicon dioxide, metal oxide activators such as zinc oxide and magnesium oxide, stearic acid, hydrocarbon softeners and extender oils, amine, ether, and phenolic antioxidants, phenylenediamine antidegradants, and tackifiers. The stocks may also contain prevulcanization inhibitors but in many stocks their use is unnecessary.

In the Examples below, cure characteristics were determined at the curing temperatures shown in the Tables by means of the Monsanto Oscillating Disc Rheometer described by Decker, Wise and Guerry in Rubber World, December 1962, page 68. From the Rheometer data, the time (t.max.) required to reach maximum torque (maximum modulus) was recorded. Vulcanisates were prepared by press curing at the selected temperature for the time indicated by the Rheometer data to give maximum cure. Other vulcanisates were prepared at the same temperature but were held at this temperature for an extended period. Both types of vulcanisate were subjected to conventional methods of physical testing.

Fatigue to Failure measurements were carried out by the method described by R. C. Ayerst, D. G. Lloyd and E. R. Rodger, Paper No. 21, DKG Meeting, Wiesbaden, May 19, 1971, and resilience measurements according to British Standard 903 Part A8 (1963). "Goodrich Flexometer" data were obtained by the method of ASTM D623-78 Method A. The base temperature for the heat build-up measurements was 50° C. and the base temperature for blow-out time measurements was 100° C.

DETAILED DESCRIPTION

Various compounds useful as vulcanisate stabilisers were prepared as follows:

Preparation (i). Decamethylene bis thiosulphate, disodium salt, dihydrate.

Sodium thiosulphate, pentahydrate (49.6 gr. 0.2 mole) and 1.10-dibromodecane (30 gr. 0.1 mole) were refluxed in a mixture of water (100 ml) and ethanol (100 ml) for 1.5 hr.

The mixture was allowed to cool and the precipitated mass was filtered. Drying in air (85° C.) afforded decamethylene bis thiosulphate as the hydrated sodium salt, with approximately two molecules of water of hydration.

A recrystallised sample gave the following elemental analysis:

| $C_{10}H_{24}Na_2O_8S_4$ | | |
| --- | --- | --- |
| | Calc. (%) | Found (%) |
| C | 26.90 | 26.79 |
| H | 5.42 | 5.09 |
| S | 28.72 | 28.74 |
| I.R. Absorption (KBr Wafer) | | |
| 3,550–3,445 $cm^{-1}$ water of crystallisation | | |
| 2,920 2,845 $cm^{-1}$ —$CH_2$— | | |
| 1,220 1,050 1,040 650 $cm^{-1}$: —S $SO_3$= | | |

Preparation (ii). Hexamethylene bisthiosulphate, disodium salt hydrate

A reaction of sodium thiosulphate with 1,6-dichlorhexane was effected by the same procedure as in Preparation (i) but with the refluxing period extended to 6 hours.

The reaction mixture was evaporated to dryness under vacuum, and the residue extracted with hot methanol. Sodium chloride was filtered off and the methanolic solution evaporated to yield hydrated hexamethylene bis thiosulphate disodium salt.

| I.R. Absorption Bands |
| --- |
| 3,555–3,455 $cm^{-1}$ Water of Crystallisation |
| 2,920 2,855 1,465 $cm^{-1}$ —$CH_2$— |
| 1,220 1,050 645 $cm^{-1}$ —S $SO_3$= |

Preparations ii (a), (b) and (c). In a similar manner to that described for hexamethylene bis (thiosulphate) disodium salt hydrate, there were prepared pentamethylene bis (thiosulphate) disodium salt hydrate, ethylene bis (thiosulphate) disodium salt hydrate, and 1,4-dimethylenecyclohexyl bis (thiosulphate) disodium salt hydrate.

Preparation (iii). Decamethylene bis(p-tolylthiosulphonate).

p-Toluenesulphinic acid, sodium salt (35.6 g; 0.2 mole) and sulphur (6.4 gr, 0.2 gr. atom) were refluxed in ethanol (50 ml) containing 0.2 ml of tetrabutylammonium hydroxide (40% aqueous solution). After 15 min. boiling, the yellow suspension became white. 1,10-Dibromodecane (30 gr, 0.1 mole) was then added and the mixture further refluxed for 3.5 hrs. The mixture was then added rapidly, with stirring, to 1 liter of ice-water to yield a precipitate which was filtered, washed with water and dried under vacuum. The product (45 g. 87.5% yield) melted at 76°–82° C.

| Elemental Analysis | (M.W. 514.75) | |
|---|---|---|
| $C_{24}H_{34}S_4O_4$ | Calc. | Found |
| C | 56.00 | 55.87 |
| H | 6.66 | 6.75 |
| S | 24.91 | 25.06 |
| Characteristic IR absorption 1.330–1,140 825 660 590 520 cm$^{-1}$ | | |

Preparation (iv) Decamethylene bis (methyl thiosulphonate)

Methyl sulphonylchloride (0.32 mole, 36.8 gr) was added dropwise to a mixture of decane-1, 10-dithiol (0.16 mole, 33.1 gr) and triethylamine (0.32 mole, 32.9 gr) in $CH_2Cl_2$ (250 ml). The temperature was maintained at $-15°$ C. throughout the addition. When addition was complete, the temperature was allowed to rise to 25° C. for 1 hr. 500 ml of water were added, the organic phase separated, dried over anhydrous sodium sulphate and evaporated under vacuum, leaving a white solid M.P. 45°–52° C.). The yield was 25.0 gr. (43%).

| Sulphur analysis: | (calculated for $C_{12}H_{26}S_4O_4$: | 35.37%) |
|---|---|---|
| | (found: | 34.90%) |

The invention is illustrated by the following Examples. In all instances, polymethylene groups $(CH_2)_x$ where x is an integer greater than 2, are linear.

EXAMPLE 1

This Example describes the production of di-n-butyl ether-4,4'-bis thiosulphate, sodium salt, $O[(CH_2)_4S_2O_3Na]_2$.

$Na_2S_2O_3.5H_2O$, (1 mole), and 250 ml of ethylene glycol were heated in a distillation apparatus fitted with a mechanical stirrer, until the temperature reached 140°–2° C. At that stage about 45 ml of water had been distilled off.

4,4'-dichlorodibutylether (0.5 mole), was then added and the mixture stirred at 125±3° C. for 25 minutes. After cooling to 80° C., the mixture was filtered to eliminate NaCl, and the filtrate poured to 3.5 liters of 2-propanol, with good stirring. The resulting slurry was cooled to $-10°$ C. and the white solid collected by filtration and dried at room temperature in a vacuum oven to constant weight. The yield of crude product is 90% of theory. The material was purified by dissolving it in 200 ml of hot methanol, filtering and pouring the filtrate into fresh 2-propanol, cooling, filtering and drying. The product then obtained had the following characteristics.

By $^1$H NMR, it contains 92% of the title compound with no significant organic or inorganic impurity excepting 8% of ethylene glycol, (probably as a co-crystallizing molecule).

$^1$H NMR: chemical shifts in ppm with dimethylsilylpropane sulphonic acid sodium salt as internal standard, in $D_2O$.

| $[NaO_3S_2\overset{1}{C}H_2(\overset{2-3}{C}H_2)_2\overset{4}{C}H_2]_2O$ | | |
|---|---|---|
| 1: | 3.12 | (T) |
| 2–3: | 1.6–1.9 | (M) |
| 4: | 3.54 | (T) |

IR spectrum in KBr showed the characteristic absorptions of thiosulphate-S-esters at 1220, 1030 and 640 Cm$^{-1}$.

EXAMPLE 2

This Example describes the production of cyclohexane-1,4-bis methylthiosulphate-S-ester, disodium salt.

$Na_2S_2O_3$-5$H_2O$ (2 mole) and 400 ml of diethyleneglycol were heated in a distillation apparatus, with stirring, until the temperature reached 132° C. 60 ml of the water had been distilled. The condenser was then fitted for reflux and 1,4-bis(chloromethyl)cyclohexane, 1 mole, was added all at once. Reflux was continued for 50 minutes. The hot mixture was then poured into 1 liter of methanol and the resulting suspension filtered whilst still hot. The filtrate was added to 4 liters of 2-propanol. Cooling, filtering and drying as in Example 1 yielded 300 gr (79% of theory) of a white powder. The crude product could be crystallized from methanol/2-propanol mixture.

$^1$H NMR: chemical shifts in ppm from dimethylsilylpropane sulphonic acid sodium salt in $D_2O$.

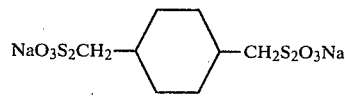

mixture of cis and trans isomers (non attributed): 1: 3.00, 3.10.

IR showed absorptions at 1220, 1035 and 645 Cm$^{-1}$ characteristic of organic ester thiosulphate.

EXAMPLE 3

This Example describes the production of $NaO_3S_2(CH_2)_3COO(CH_2)_4S_2O_3Na$.

This compound was prepared by a procedure similar to that described in Example 1, but using $Cl(CH_2)_3COO(CH_2)_4Cl$ in place of 4,4'-dichlorodibutyl ether. The dichlorocompound was prepared by the reaction of 4-chlorobutyryl chloride with tetrahydrofuran in the presence of zinc chloride. The period of reaction after addition of the dichlorocompound to the thiosulphate solution at 125° C. was 0.5 hours, and the yield was 80% of crude product containing 83% of the disodium salt and 12% of ethylene glycol (by $^1$H NMR).

$^1$H NMR: chemical shifts in ppm from dimethylsilylpropane sulphonic acid sodium salt, in $D_2O$.

| $\overset{1}{\text{NaO}_3\text{S}_2\text{CH}_2}\overset{2}{\text{CH}_2}\overset{3}{\text{CH}_2}\text{COO}\overset{4}{\text{CH}_2}(\overset{5\text{-}6}{\text{CH}_2})_2\overset{7}{\text{CH}_2}\text{S}_2\text{O}_3\text{Na}$ | | |
|---|---|---|
| 1,7: | 3.12 | (T) |
| 3: | 2.55 | (T) |
| 4: | 4.16 | (T) |
| 2,5,6: | 1.7–2.2 | (M) |

EXAMPLE 4

This Example describes the production of $\text{NaO}_3\text{S}_2(\text{CH}_2)_5\text{COO}(\text{CH}_2)_4\text{S}_2\text{O}_3\text{Na}$.

This compound was prepared by a procedure similar to that described in Example 1, but using $\text{Cl}(\text{CH}_2)_5\text{COO}(\text{CH}_2)_4\text{Cl}$ in place of 4,4'-dichlorodibutyl ether. The dichlorocompound was prepared by the reaction of thionyl chloride with epsilon-caprolactam in the presence of zinc chloride, giving a reaction mixture containing 6-chlorohexanoyl chloride, to which tetrahydrofuran was then added. The final reaction mixture was washed with aqueous sodium carbonate solution, and the required dichloro-compound was isolated by distillation of the organic phase after drying.

In the reaction of the dichloro-compound with sodium thiosulphate, the yield was 75% of theory of a product containing 85% of the disodium salt and 15% of ethylene glycol.

| $\text{NaO}_3\text{S}_2\text{CH}_2(\text{CH}_2)_3\text{CH}_2\text{COOCH}_2(\text{CH}_2)_2\text{CH}_2\text{S}_2\text{O}_3\text{Na}$ | | |
|---|---|---|
| 1,9: | 3.11, 3.13 | (T) |
| 2–4, 7–8: | 1.3–1.9 | (M) |
| 5: | 2.42 | (T) |
| 6: | 4.16 | (T) |

EXAMPLE 5

This Example describes the production of $\text{NaO}_3\text{S}_2(\text{CH}_2)_3\text{COO}(\text{CH}_2)_6\text{OOC}(\text{CH}_2)_3\text{S}_2\text{O}_3\text{Na}$.

This compound was prepared by a procedure similar to that of Example 1, but using $\text{Cl}(\text{CH}_2)_3\text{COO}(\text{CH}_2)_6\text{OOC}(\text{CH}_2)_3\text{Cl}$ in place of 4,4'-dichlorodibutyl ether. The dichlorocompound was prepared by the reaction of 1,6-hexanediol with 4-chlorobutyryl chloride.

Reaction of the dichloro-compound with sodium thiosulphate and processing of the reaction mixture by the procedure of Example 1 gave a 30% yield of a product containing 83% of the above-identified sodium salt and 8% of ethylene glycol.

$^1$H NMR: chemical shifts in ppm from dimethylsilylpropane sulphonic acid sodium salt, in D$_2$O.

| $[\text{NaO}_3\text{S}_2\overset{1}{\text{CH}_2}\overset{2}{\text{CH}_2}\overset{3}{\text{CH}_2}\text{COO}\overset{4}{\text{CH}_2}\overset{5}{\text{CH}_2}\overset{6}{\text{CH}_2}]_2$ | | |
|---|---|---|
| 1: | 3.14 | (T) |
| 2: | 1.67 | (M) |
| 3: | 2.55 | (T) |
| 4: | 4.15 | (T) |
| 5: | 2.09 | (M) |
| 6: | 1.40 | (M) |

EXAMPLE 6

This Example describes the production of $\text{NaO}_3\text{S}_2(\text{CH}_2)_{10}\text{COO}(\text{CH}_2\text{CH}_2\text{O})_3\text{OC}(\text{CH}_2)_{10}\text{S}_2\text{O}_3\text{Na}$.
This compound was prepared by a procedure similar to that of Example 2, but using $\text{Br}(\text{CH}_2)_{10}\text{COO}(\text{CH}_2\text{CH}_2\text{O})_3\text{OC}(\text{CH}_2)_{10}\text{Br}$ in place of 1,4-bis(chloromethyl)-cyclohexane. The dibromo-compound was prepared by the esterification of triethylene glycol with 11-bromoundecanoic acid. Reaction of the dibromo-compound with sodium thiosulphate gave a 60% yield of a product containing 3.5% of diethyleneglycol.

$^1$H NMR: chemical shifts in ppm with dimethylsilylpropane sulphonic acid sodium salt, in D$_2$O

| $[\text{NaO}_3\text{S}_2\text{CH}_2(\text{CH}_2)_8\text{CH}_2\text{COOCH}_2\text{CH}_2\text{OCH}_2]_2$ | | |
|---|---|---|
| 1: | 3.10 | (T) |
| 2–9: | 1.2–1.8 | (M) |
| 10: | 2.38 | (T) |
| 11: | 4.27 | (M) |
| 12: | 3.76 | (M) |
| 13: | 3.69 | (S) |

EXAMPLE 7

This Example describes the preparation of $\text{NaO}_3\text{S}_2(\text{CH}_2)_{10}\text{COO}(\text{CH}_2\text{CH}_2\text{O})_2\text{OC}(\text{CH}_2)_{10}\text{S}_2\text{O}_3\text{Na}$.
This compound was prepared by a procedure similar to that of Example 2, but using $\text{Br}(\text{CH}_2)_{10}\text{COO}(\text{CH}_2\text{CH}_2\text{O})_2\text{OC}(\text{CH}_2)_{10}\text{Br}$ in place of 1,4-bis(chloromethyl)-cyclohexane. The dibromo-compound was prepared by esterifying diethylene glycol with 11-bromoundecanoic acid. Reaction of the dibromo-compound with sodium thiosulphate gave an 80% yield of product containing 6.5% of diethylene glycol.

$^1$H NMR: chemical shifts in ppm with dimethylsilylpropane sulphonic acid sodium salt, in D$_2$O–CD$_3$OD.

| $[\text{NaO}_3\text{S}_2\overset{1}{\text{CH}_2}(\overset{2\text{-}9}{\text{CH}_2})_8\overset{10}{\text{CH}_2}\text{C}\overset{11}{\text{OOCH}_2}\overset{12}{\text{CH}_2}]_2\text{O}$ | | |
|---|---|---|
| 1: | 3.10 | (T) |
| 2–9: | 1.2–1.8 | (M) |
| 10: | 2.38 | (T) |
| 11: | 4.26 | (M) |
| 12: | 3.78 | (M) |

EXAMPLE 8

This Example describes the production of $\text{NaO}_3\text{S}_2(\text{CH}_2)_4\text{OCH}_2\text{O}(\text{CH}_2)_4\text{S}_2\text{O}_3\text{Na}$.

This compound was prepared by a procedure similar to that of Example 1, but using 4,4'-dichlorobutyl formal in place of 4,4'-dichlorodibutyl ether. 4,4'-dichlorobutyl formal was prepared from formaldehyde, HCl and tetrahydrofuran. The reaction of sodium thiosulphate with 4,4-dichlorobutyl formal gave an 80% yield of a product containing 13% of ethylene glycol.

$^1$H NMR: chemical shifts in ppm with dimethylsilylpropane sulphonic acid sodium salt, in D$_2$O.

| $[\text{NaO}_3\text{SS}\overset{1}{\text{CH}_2}(\overset{2\text{-}3}{\text{CH}_2})_2\overset{4}{\text{CH}_2}\text{O}]_2\overset{5}{\text{CH}_2}$ | | |
|---|---|---|
| 1: | 3.16 | (T) |
| 2–3: | 1.62, 1.90 | (M) |
| 4: | 3.68 | (T) |
| 5: | 4.78 | (S) |

EXAMPLE 9

This Example describes a general procedure for the preparation of new compounds of the invention that are nickel or cobalt salts.

200 Gr. of commercial cation exchange resin in the H$^+$ form is placed in a glass column and treated with a solution of 60 gr. of NiSO₄6H₂O or CoCl₂.6H₂O in 100 ml of water. The column is then washed with distilled water until the eluate is colourless and neutral. A solution of 10 gr. of the bisthiosulphate sodium salt in 100 ml. of water is then slowly passed through the column, followed by 100 ml of distilled water. The eluate is evaporated under vacuum, giving a quantitative yield of the nickel or cobalt salt based on the sodium salt. By the procedure, there are prepared the following nickel and cobalt salts.

O[(CH₂)₄S₂O₃]₂Ni  O[(CH₂)₄S₂O₃]₂Co
CH₂[O(CH₂)₄S₂O₃]Ni  CH₂[O(CH₂)₄S₂O₃]Co
C₆H₁₀(CH₂S₂O₃)₂Ni  C₆H₁₀(CH₂S₂O₃)₂Co
[O₃S₂(CH₂)₃COO(CH₂)₄S₂O₃]Ni [O₃S₂(CH₂)₃COO(CH₂)₄S₂O₃]Co
[O₃S₂(CH₂)₅COO(CH₂)₄S₂O₃]Ni [O₃S₂(CH₂)₅COO(CH₂)₄S₂O₃]Co
[O₃S₂(CH₂)₃COO(CH₂)₆OOC(CH₂)₃S₂O₃]Ni
[O₃S₂(CH₂)₃COO(CH₂)₆OOC(CH₂)₃S₂O₃]Co
[O₃S₂(CH₂)₁₀COO(CH₂CH₂O)₃OC(CH₂)₁₀S₂O₃]Ni
[O₃S₂(CH₂)₁₀COO(CH₂CH₂O)₃OC(CH₂)₁₀S₂O₃]Co
[O₃S₂(CH₂)₁₀COO(CH₂CH₂O)₂OC(CH₂)₁₀S₂O₃]Ni
[O₃S₂(CH₂)₁₀COO(CH₂CH₂O)₂OC(CH₂)₁₀S₂O₃]Co

Also prepared by the above procedure are:

[O₃S₂(CH₂)₅S₂O₃]Ni  [O₃S₂(CH₂)₅S₂O₃]Co
[O₃S₂(CH₂)₆S₂O₃]Ni  [O₃S₂(CH₂)₆S₂O₃]Co
[O₃S₂(CH₂)₈S₂O₃]Ni  [O₃S₂(CH₂)₈S₂O₃]Co
[O₃S₂(CH₂)₁₀S₂O₃]Ni  [O₃S₂(CH₂)₁₀S₂O₃]Co
[O₃S₂(CH₂)₁₂S₂O₃]Ni  [O₃S₂(CH₂)₁₂S₂O₃]Co

EXAMPLE 10

This Example describes the preparation of hexamethylene bis (thiosulphate) potassium salt.

A mixture of 1,6-dichlorohexane (54.6 g, 0.35 mol) and K₂S₂O₃H₂O (163.4 g. 0.75 mol) in a mixture of water (230 ml) and ethanol (230 ml) was heated in an autoclave at 135° C. for 8 minutes. The solution thus obtained was filtered while still hot, and the filtrate was cooled to −10° C. to yield a solid which was collected by centrifuging. The solid was recrystallised from 250 ml. aqueous ethanol to give 98 g of hexamethylene bis(thiosulphate) potassium salt.

EXAMPLE 11

This Example describes the preparation of hexamethylene bis(thiosulphate) barium salt.

A hot solution of barium chloride (BaCl₂2 H₂O; 217 g) in water (450 ml) was added slowly to a hot solution of hexamethylene bis(thiosulphate) sodium salt (300 g as dihydrate) in water (450 ml) with stirring over 50 min. The solution was cooled to yield a solid which was collected by filtration and dried (308 g; 81.7% yield). The barium content (by gravimetry) corresponded to 97.5% of [(CH₂)₃S₂O₃]₂Ba 2H₂O, and the sodium content was 2% calculated as NaCl.

EXAMPLE 12

This Example describes the preparation of (A) hexamethylene bis(thiosulphate) cobalt salt, and (B) decamethylene bis(thiosulphate) diammonium salt. (A) Hexamethylene bis(thiosulphate)barium salt (135 g, 0.276 mole) was dissolved in 1,350 ml of water. CoSO₄ 7 H₂O (101 g, 0.276 mole) in 150 ml H₂O was added over 35 minutes to the well stirred barium salt solution. The resulting slurry was agitated for two hours. Filtration, followed by evaporation of the filtrate afforded a pink solid: 131.2 g.

Elemental analysis: Found: C 14.44%, H 4.18%, S 25.60%, Co 11.88%, Na 1.97%.

This analysis corresponds closely with that calculated for hexamethylene bis(thiosulphate) cobalt salt hexahydrate (C₆H₂₄O₁₂S₄Co) contaminated with 5% by weight NaCl.

(B) Decamethylene bis(thiosulphate)diammonium salt was prepared from decamethylene bis(thiosulphate) barium salt (itself prepared from decamethylene bis(thiosulphate) disodium salt by a procedure similar to that of Example 11) by essentially the same method as that described in Part (A) but using ammonium sulphate in place of cobalt sulphate.

Elemental analysis: Calculated: C 29.98, H 7.04, N 6,99, S 32.01. Found: C 29.81 H 7.15, N 6.84, S 31.83.

EXAMPLE 13

Hexamethylene bis(thiosulphate) nickel salt was prepared from hexamethylene bis(thiosulphate) barium salt by essentially the same procedure as that described in Example 12 but using NiSO₄6H₂O in place of Co SO₄7-H₂O. The yield was 131.3 g.

Elemental analysis: Found: C 14.42%, H 3.93%, S 25.32%, Ni 11.90%, Na 2.04%.

This analysis corresponds closely with that calculated for hexamethylene bis(thiosulphate) nickel salt hexahydrate (C₆H₂₄O₁₂S₄Ni) contaminated with 5.2% by weight NaCl.

EXAMPLE 14

Various metal salts were prepared by passing an aqueous solution of hexamethylene bis(thiosulphate) sodium salt through a column of cation exchange resin in the form of the desired cation salt, and evaporating the percolate to dryness. Under the conditions employed, cation exchange was incomplete, and products having the following compositions by weight were obtained (HTSNa=hexamethylene bis(thiosulphate) sodium salt):

(A) Hexamethylene bis(thiosulphate) zinc salt 97.5%, HTSNa 2.5%

(B) Hexamethylene bis(thiosulphate) magnesium salt 82.5%, HTSNa 17.5%, (C) Hexamethylene bis(thiosulphate) calcium salt 91.9%, HTSNa 8.1%.

Hexamethylene bis(thiosulphate) lithium salt (D) was also prepared by cation exchange from the sodium salt. It was found possible to purify the lithium salt by recrystallisation from a mixture of equal volumes of propanol and toluene, a solvent in which HTSNa is insoluble.

EXAMPLE 15

This Example describes the preparation of compounds where m in the general formula represents a substituted ammonium ion.

(A) N-(1,1,3,3-tetramethylbutyl)benzylamine (8.8 g, 0.04 mole) in 200 ml of water-methanol (1/1) mixture was treated with HCl (to pH 4). To the resulting clear solution was added hexamethylene bis(thiosulphate) sodium salt dihydrate (7.8 g, 0.02 mole) in 100 ml H₂O. The resulting slurry was cooled to 0° C. and filtered. The product was washed with water and dried. Yield: 13.6 g (87%) of hexamethylene bis(thiosulphate) N-(1,1,2,3-tetramethylbutyl)-N-benzylammonium salt, m.p. 149°–151° C.

Analysis: Found: C 57.81, H 8.43, N 3.66, S 17.30. Calculated for $C_{36}H_{62}N_2O_6S_4$: C 57.71, H 8.61 N 3.74, S 17.12.

(B) N-tert-butylbenzylamine (0.2 mole, 32.6 g) was treated in 200 ml of water with dilute HCl (to pH 5). Hexamethylene bis(thiosulphate) sodium salt dihydrate (0.1 mole, 39 g) in 400 ml $H_2O$ was added, and the volume of the resulting solution was reduced by evaporation to about 200 ml. The precipitate which formed was collected and dried at room temperature under vacuum. Yield: 60 g (95%) of hexamethylene bis(thiosulphate)N-tert-butyl-N-benzylammonium salt.

(C) N-isopropyl-N'-phenyl-p-phenylenediamine (226 g. 1 mole) was dissolved in ethanol (500 ml), and $H_2SO_4$ (96%, 51 g, 0.50 mole) dissolved in 100 ml EtOH, was added dropwise to the stirred amine solution. The sulphate which precipitated was collected by filtration, washed with ethanol and dried (258 g, 94% yield).

The above sulphate (27 g, 0.1 mole) was dissolved in methanol (300 ml), and hexamethylene bis(thiosulphate) sodium salt dihydrate (19.5 g, 0.15 mole) in 600 ml of warm methanol was added. The precipitated $Na_2SO_4$ was filtered off, and the filtrate was evaporated to dryness under vacuum. Yield: 34 g, (92%) of hexamethylene bis(thiosulphate) N-isopropyl-N'-(p-phenylaminophenyl) ammonium salt.

(D) 1,4-bis(chloromethyl)cyclohexane (0.165 mole), sodium thiosulphate pentahydrate (0.369 mole) sodium sulfite (6.1 g), methanol (150 ml) and water (150 ml) were charged into an autoclave and heated at 135° C. for 45 minutes. To the cooled reaction mixture, which was a solution of 1,4-dimethylcyclohexane-α, α-bis (thiosulphate) sodium salt, 400 ml of water was added. N-tert-butylbenzylamine (0.306 mole) in 150 ml methanol and 850 ml $H_2O$ was adjusted with concentrated HCl to pH4, and the resulting solution was added with stirring to the thiosulphate solution. The white precipitate was filtered, washed with water and dried. Yield: 92 g, (91%) of 1,4-dimethylcyclohexane-α, α-bis(thiosulphate) N-tert-butyl, N-benzylammonium salt.

EXAMPLE 16

This Example describes the preparation of compounds where M in the general formula represents an ion derived from a cation-forming organic nitrogenous base other than a simple amine.

(A) Dibromohexane (24.3 g, 0.1 mole) and thiourea (15.2 g, 0.2 mole) were refluxed for two hours in 200 ml of ethanol. 200 ml of water was added and the resulting solution cooled down to room temperature. Hexamethylene bis(thiosulphate) sodium salt dihydrate (39 g, 0.1 mole) in 100 ml $H_2O$ was added dropwise with good stirring.

The resulting slurry was cooled down to 0° C. and filtered. The filter cake was washed with ice-water and dried to give 50.1 g (92% yield) of hexamethylene bis(thiosulphate) 1,6-bis(isothiouronium) hexane salt.

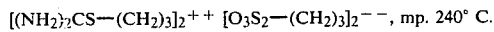, mp. 240° C.

Analysis: Found: C 30.87, H 5.92, N 10.28, S 35.31 Calculated for $C_{14}H_{32}N_4O_6S_6$ C 30.41, H 5.58, N 9.58, S 32.79.

(B) 10.2 g (0.1 mole) of 96% $H_2SO_4$ were added to a solution of 2,2,4-trimethyl-1-2-dihydroquinoline (34.6 g, 0.2 mol) in 300 ml methanol. To this solution, a solution of hexamethylene bis(thiosulphate) sodium salt dihydrate (39 g, 0.1 mol) in 300 ml hot methanol wass added slowly. The precipitated sodium sulphate was filtered off and the filtrate was evaporated to dryness giving 45 g of hexamethylene bis(thiosulphate) 2,2,4-trimethyl-1,2-dihydroquinolinium salt.

(C) A glass column was loaded with 300 g of strong acid ion exchange resin (1.8 me/ml) to which was added a solution of 30 g of guanidinium hydrochloride in 150 ml water. The column was washed with 300 ml distilled water. A solution of 35 g of hexamethylene bis (thiosulphate) sodium salt in 400 ml water was then passed through the column and the percolate was evaporated to dryness. The recovered solid

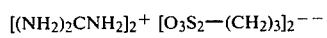

57.5 g (79.2%) had m.p. 172°–175° C.

Analysis: Found: C 22.24, H 5.33, N 19.80, S 27.56. Calculated for $C_8H_{24}N_6S_4O_6$ C 22.43, H 5.61, N 19.83, S 29.91.

(D) A solution of hexamethylene bis (thiosulphate) sodium salt (100 g. 0.282 mol) in 500 ml of water at 70° C. was added slowly to a stirred solution of 133 g (0.568 mol) of diphenylguanidine hydrochloride in 700 ml water. The mixture was cooled and the solid which separated was collected. Recrystallisation from a mixture of equal parts by volume of methanol and toluene gave 154 g (77.1%) of hexamethylene bis (thiosulphate) bis (diphenylguanidinium) salt, m.p. 151°–153° C.

Analysis: Found: C 52.25, H 5.54, N 11.39, S 17.38. Calculated for $C_{32}H_{36}N_6S_4O_6$: C 50.85, H 5.65, N. 11.86, S 18.08.

(E) N,N'-Di(1,4-dimethylpentyl)-p-phenylenediamine (3.04 g; 0.01 mole) was dissolved in isopropyl alcohol (50 ml) and treated with 1.02 g of 96% $H_2SO_4$ (0.01 mole). The resulting precipitate was filtered, and after washing with isopropyl alcohol, it was dissolved in methanol (50 ml). The solution thus obtained was mixed with a methanolic solution of hexamethylene bis thiosulphate, sodium salt (4.1 g of a 86% purity product, 0.01 mole). The precipitate which formed ($Na_2SO_4$) was filtered off and the resulting clear solution evaporated to dryness. The residue was crystallized from absolute ethanol to give 2.1 g, (34%) of the N,N'-di(1,4-dimethylpentyl)-p-phenylenediamine salt of hexamethylene bis thiosulphate.

| I. R. spectrum: | 3,450 cm$^{-1}$ NH | | |
|---|---|---|---|
| 1,940 | 1,590 | 1,520 cm$^{-1}$ | |
| 1,240 | 1,170 | 1,030 | 640 cm$^{-1}$ —$S_2O_3$ |

[1]NHMR confirmed the 1:1 ratio of amine-hexamethylene bis thiosulphate moieties.

(F) A solution of benzylisothiouronium chloride (40.5, 0.2 mole) in 100 ml of water/ethanol (1/1) was added to a solution of hexamethylene bis thiosulphate sodium salt (41 g of 86% purity, 0.1 mole) in 100 ml $H_2O$. The precipitate which formed immediately was stirred for 0.5 hour at room temperature, then filtered off and dried under vacuum to give 57.3 g. (89.1%) of hexamethylene bis thiosulphate bis benzylisothiouronium salt, m.p. 133°–135° C.

| I. R. spectrum: | 1,215 1,170 1,025 645 cm$^{-1}$ Thiosulphate |
|---|---|
| | 1,670 720 700 cm$^{-1}$ Benzylisothiouronium |

¹HNMR confirms the 1:2 ratio of hexamethylene bis thiosulphate to benzylisothiouronium.

EXAMPLE 17

This Example describes the preparation of di-n-hexyl-sulphone-6, 6'-bis(thiosulphate) sodium salt NaO₃S-2—(CH₂)₆SO₂(CH₂)₆S₂O₃Na.

The overall route was:

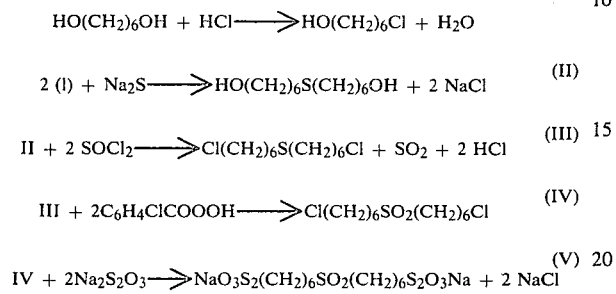

Procedures

Compound I was prepared according to Organic Synetheses, Coll. Vol. 3, p. 446-448.

Compound II was prepared from I, (0.3 moles 42 g) and Na₂S 9H₂O (0.15 mole: 36 g) dissolved in 60 ml H₂O and 60 ml EtOH.

The mixture was refluxed with stirring for ca. 18 hrs. The solution was evaporated under vacuum and the residue extracted with 130 ml of ether in two portions. The combined extracts were dried and evaporated. The residue was crystallized twice from petrol/1-toluene/2, yield 16.8 g, 48%, m.p. 46°–48° C.

A repeat preparation yielded a crude product (89%), m.p. 43°–46° C., which on recrystallisation gave a yield of 71%, m.p. 50°–51° C.

Compound III was prepared from II, (135 g, 0.57 mole) and pyridine (5 ml) stirred in a flask fitted with reflux condenser to which CHCl₃ (1000 ml) was added, followed by the dropwise addition of SOCl₂ (107 ml) over 50 minutes.

The mixture was kept at 40° C. for 5 hrs. Water (200 ml) was cautiously added to the cooled mixture. Work-up of the organic layer afforded oily liquid (175 g), which by distillation at 0.07 mm Hg gave 81 g (52.4%) of III distilling at 158°–160° C.

Compound IV was prepared from III (20 g; 0.074 mole) in CH₂Cl₂ (150 ml) by treatment at 35° C. (under reflux) with 85% meta-chloroperbenzoic acid (37.5 g, 0.185 mole) in ether (150 ml) over 1.75 hr.

The resulting mixture was washed with 2 M NaOH (200 ml), the organic layer evaporated under vacuum (crude yield 22.3 g, 100%, m.p. 45°–51° C.) and the residue crystallized from toluene-petrol ½. Yield 18.6 g (83%) m.p. 50°–52° C.

Compound IV (15.4 g, 0.05 mole), Na₂S₂O₃5H₂O (25 g; 0.1 mole), water (50 ml) and methanol (25 ml) were charged to an autoclave and heated to 135° C. for 20 min. The mixture was filtered hot and the filtrate was cooled to −30° C. Compound V crystallised from the solution and was collected by centrifugation. Yield: 18.8 g.

EXAMPLE 18

This Example describes the preparation of a compound in which two thiosulphate radicals are linked by a bridging group containing nitrogen.

(a) Preparation of NH₂⁺[(CH₂)₆Cl]₂Cl⁻. 6-Bromohexanol (100 g, 0.553 mole) and concentrated ammonia (390 ml, 2.75 mole) were heated to 100° C. in an autoclave for 1 hour. The cooled mixture was evaporated to dryness under vacuum and 220 ml of 2.5 N NaOH (0.55 mole) were added.

6-Bromohexanol (0.55 mole) was added to the above solution, and the mixture was boiled under reflux for 2 hours. Water was removed by evaporation and the residue neutralised with NaOH (0.55 mole) as above. An organic phase consisting essentially of NH[(CH₂)₆OH]₂ separated and was collected.

NH[(CH₂)₆OH]₂ (32.6 g, 0.15 mol) was added over 1.25 hours to SO Cl₂ (42.8 g) in CHCl₃(30 ml). The solution was kept overnight and then refluxed for 30 minutes. CHCl₃ was evaporated giving 32.9 g (75.5%) ⁺NH₂[(CH₂)₆Cl]₂Cl⁻.

(b) Preparation of bis(thiosulphate). A mixture of ⁺NH₂[(CH₂)₆Cl]₂Cl⁻ (25 g, 0.086 mol) and Na₂S₂O₃5-H₂O (42.6 g, 0.172 mol) in 80 ml H₂O and 50 ml methanol was heated at 130° C. for 7 minutes in an autoclave. The resulting solution was evaporation to dryness and the residue was extracted with hot methanol. Evaporation of the extract gave 35.6 g (88.6%) of ⁺NH₂[(CH₂)₆S₂O₃Na]₂Cl⁻ as a white solid (main I.R. absorptions were those of organic thiosulphate esters: 1,200 1,025 640 cm⁻¹).

Analysis: Found: C 30.08, H 5.56, N 2.67, S 25.66 Calculated for C₁₂H₂₆NS₄O₆Na₂Cl C 30.85, H 5.61, N 3.00, S 27.46

EXAMPLE 19

This Example describes the preparation of a compound containing three thiosulphate radicals linked through an organic bridging group containing nitrogen.

NH[(CH₂)₆OH]₂ (40 g), prepared as described in the previous Example, was reacted with 6-bromohexanol (18.2 g) by heating in 50 ml butanol under reflux (105° C.) for 2 hours. Butanol was then evaporated under vacuum, and the resulting oil neutralized with NaOH and distilled under vacuum. The main fraction, distilling at ≃190° C. was found by NMR to be essentially pure tri(6-hydroxyhexyl) amine.

N[(CH₂)₆OH]₃, (25 g, 0.055 mole) was added over 1.25 hour to SOCl₂ (24 g, 0.2 mole) in CHCl₃ (25 ml). The solution was kept overnight and then refluxed for 30 minutes. CHCl₃ was evaporated, and the residue used as such in the following stage: 12 g were reacted with Na₂S₂O₃5H₂O (20 g) in H₂O (40 ml) and methanol (20 ml) for 5 minutes at 135° C. in an autoclave. The cooled solution was treated with charcoal, filtered, and the filtrate was evaporated. The residue was extracted with hot methanol, and the extract, after filtration, was evaporated to yield 14.6 g, (71%) of an off-white solid. I. R. showed disappearance of CH₂Cl absorption band, and presence of organic thiosulphate absorption bands. Na⁺ analysis is in agreement with general structure:

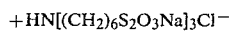

+HN[(CH₂)₆S₂O₃Na]₃Cl⁻

EXAMPLE 20

This Example describes the preparation of a compound containing four thiosulphate groups.

(a) 6-bromohexanoic acid (72.4 g, 0.37 mole) and pentaerythritol (12.25 g, 0.088 mole) were refluxed in toluene, in a Dean and Stark device for two hours in the presence of 6 ml H₂SO₄. The black solid which separated was filtered off and the solution neutralised with aqueous caustic. Separation, washing and evaporation of the organic phase afforded 45 g. of an oil consisting mainly of C[CH$_2$OCO(CH$_2$)$_5$Br]$_4$ showing I.R. absorptions as follows C=O ester: 1,720 cm$^{-1}$. CH$_2$Br: 730 640 560 cm$^{-1}$.

(b) The above tetrabromide (30 g, 0.035 mole) and Na$_2$S$_2$O$_3$ 5H$_2$O (33.5 g, 0.135 mole) dissolved in 50 ml H$_2$O–50 ml ethanol were heated to 135° C. for 5 min. in an autoclave.

After cooling, the reaction liquor was treated with active charcoal, filtered and evaporated. The residue was extracted with methanol (150 ml) and the solution poured into 800 ml of isopropanol. The slurry was cooled down to −10° C. and filtered. The dried product, C[CH$_2$OCO(CH$_2$)$_5$S$_2$O$_3$Na]$_4$ weighed 27 g (72.5% yield).

EXAMPLE 21

This Example describes the preparation of polythiosulphates.

(a) 6-bromohexanoic acid (45 g, 0.23 mole) in 200 ml CH$_2$Cl$_2$ was treated with SOCl$_2$ (35 g, 0.295 mole) in a flask fitted with a gas outlet through an efficient condenser. The reaction was left overnight. The resulting solution was then added to a suspension of polyvinyl alcohol (38 g of 75% hydrolysed PVA, MW 2,000) in CH$_2$Cl$_2$(300 ml).

The reaction was allowed 2 days at room temperature to achieve completion. The resulting solution was evaporated to dryness, redissolved in 100 ml CH$_2$Cl$_2$ and precipitated in 500 ml of diethylether to remove any 6-bromohexanoic acid. The average formula of the so-obtained polymer was approximately:

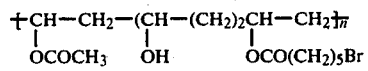

(b) 35 g of the above polymer was added to a 1/1 water-methanol solution of 40 g Na$_2$S$_2$O$_3$ 5H$_2$O. The mixture was refluxed for 1.5 hour, (until it became homogenous). Evaporation to dryness, followed by extraction with absolute methanol afforded a solution which was allowed to evaporate as a film on a large dish. Yield: 24 g of a rubber-like translucent polymer. I.R. showed the usual organic thiosulphate absorption bands 1,200 1,040 640 cm$^{-1}$.

B. (a) Preparation of poly(1-chloro-2,3-epoxy-propane). Epichlorohydrin (0.2 mole; 18.5 g) was carefully added to AlCl$_3$ (0.023 mole; 3.1 g) in 10 ml of dired nitrobenzene. 20 ml of water were added to the reaction mixture, and the organic layer was decanted and dried over CaSO$_4$. The solvent was removed and the brown liquid residue (13.9 g) was washed with petroleum ether to eliminate the last traces of nitrobenzene.

(b) Preparation of polythiosulphate. A mixture of sodium thiosulphate (0.15 mole; 37.5 g) and ethylene glycol (1.34 mole; 75 ml) was heated to 130° C.–140° C., and water was distilled off. After cooling to 120° C., 13.9 of the polyepichlorohydrin from (a) was added over a period of 5 minutes and the reaction mixture was stirred for 15 minutes at 120°–125° C. The reaction mixture was then cooled and filtered to remove NaCl. The filtrate was poured into 1 liter of well stirred isopropanol, and a solid precipitated. This was filtered and recrystallised from a methanol/isopropanol (500 ml/1000 ml) mixture, to give, after drying, 20.5 g. of a polymer of units

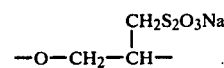

as a brown solid.

EXAMPLE 22

This Example illustrates the uxse of vulcanisation stabilisers according to this invention in natural rubber vulcanisates.

A masterbatch having the following composition was prepared:

|  | Parts by Weight |
| --- | --- |
| Natural rubber | 100 |
| Carbon Black | 50 |
| Zinc Oxide | 5 |
| Stearic Acid | 2 |
| Processing Oil | 3 |
| N—phenyl-N'—(1,3-dimethylbutyl)-p-phenyl-enediamine(Antidegradant) | 2 |

Portions of the masterbatch were taken and mixed with sulphur, 2(morpholinothio) benzothiazole and the stabiliser compound in the proportions 2.5, 0.7 and 3.0 parts by weight respectively per 100 parts by weight of rubber. The stabiliser was actually introduced into the mixture as a suspension of finely-ground solid in an equal weight of processing oil. A further portion of masterbatch to which only sulphur and 2(morpholinothio) benzothiazole were added was used as a control.

The curing characteristics of the vulcanisable compositions thus obtained and the physical properties of the vulcanisates were determined as described above.

The results are given in Table 1 below in which A is decamethylene bis(thiosulphate) disodium salt hydrate B is hexamethylene bis(thiosulphate) disodium salt hydrate C is pentamethylene bis(thiosulphate) disodium salt hydrate E is cyclohexylene-1,4-dimethylene bis(thiosulphate) disodium salt hydrate.

TABLE 1

|  | None | | Stabiliser Compound | | | | | | | | |
| --- | --- | --- | --- | --- | --- | --- | --- | --- | --- | --- | --- |
|  |  |  | A | | B | | C | | D | | E |
| Cure time at 140° C. (mins.) | 40 | 200 | 60 | 200 | 60 | 200 | 60 | 200 | 60 | 200 | 60 | 200 |
| 300% modulus (MPa) | 14.0 | 11.0 | 14.4 | 14.2 | 13.3 | 12.7 | 13.9 | 13.3 | 15.4 | 14.0 | 13.9 | 12.7 |
| Fatigue-toFailure kilocycles at 1 MPa strain energy | 129 | 84 | 151 | 121 | | | | | | | | |
| % retention of modulus during overcure | 78.6 | | 98.6 | | 95.5 | | 95.7 | | 91.0 | | 91.4 | |
| % decrease in | 35 | | 20 | | | | | | | | | |

TABLE 1-continued

| | Stabiliser Compound | | | | |
|---|---|---|---|---|---|
| | None | A | B | C | D | E |
| flex-life resulting from overcure | | | | | | |

The beneficial effect of the stabiliser compounds on the ageing effect commonly referred to as "reversion" is shown by comparison of the percentage retention of 300% modulus during overcure of the samples containing stabiliser compounds with that of the control. The beneficial effect on flex-life of the presence of a stabiliser compound is also apparent.

EXAMPLE 23

This Example illustrates the use of a vulcanisation stabiliser according to this invention in a blend of natural rubber and butadiene rubber.

A masterbatch having the following composition was prepared:

| | Parts by Weight |
|---|---|
| Natural rubber | 70 |
| Butadiene rubber | 30 |
| Carbon Black | 50 |
| Zinc Oxide | 5 |
| Stearic Acid | 2 |
| Processing Oil | 6 |
| N—phenyl-N'—(1,3-dimethyl-butyl)-p-phenylenediamine (Antidegradant) | 2 |

A portion of the masterbatch was taken and mixed with sulphur and 2(morpholinothio) benzothiazole in the proportions 2.5 and 0.7 parts by weight respectively per 100 parts by weight of rubber to give a control. A further portion was mixed with the same amounts of sulphur and 2(morpholinothio) benzothiazole and with 3.0 parts by weight of decamethylene bis(thiosulphate) disodium salt hydrate, (A), introduced as a dispersion of the finely-powdered solid in an equal weight of processing oil.

The curing characteristics of the vulcanisable compositions thus obtained and the physical properties of the vulcanisates were determined as described above.

The results are given below.

| | Stabiliser Compound | | | |
|---|---|---|---|---|
| | None | | A | |
| Cure time at 140° C. (mins.) | 50 | 200 | 60 | 200 |
| 300% modulus (MPa) | 126 | 111 | 122 | 126 |

The beneficial effect on reversion is shown by comparison of the 300% modulus figures. For the control the modulus after 200 minutes cure had fallen to 88% of the maximum modulus, while the 300% modulus of the mixture containing the stabiliser compound cured for 200 minutes was slightly higher than the modulus after 60 minutes cure (indicated by the Rheometer to be the time to maximum modulus).

EXAMPLE 24

A control sample and samples containing 3.0 parts by weight of stabiliser compound were prepared from a masterbatch as in Example 1. Results of tests are given in Table 2 below in which F is decamethylene bis(-methyl thiolsulphonate) and G is decamethylene bis(p-tolyl thiolsulphonate).

TABLE 2

| | Stabiliser Compound | | | | | |
|---|---|---|---|---|---|---|
| | None | | F | | G | |
| Cure time at 140° C. (mins.) | 40 | 200 | 60 | 200 | 60 | 200 |
| 300% modulus (MPa) | 16.0 | 13.5 | 17.7 | 18.1 | 17.9 | 17.5 |
| Resilience (%) | 68.9 | 57.9 | 68.6 | 61.2 | — | |
| % retention of modulus during overcure | 84 | | 102 | | 98 | |
| % retention of resilience during overcure | 84 | | 89 | | — | |

The beneficial effect of the stabilisers on modulus is apparent from the figures. The resilience figures show that this property is less affected by overcure in the presence of the stabiliser than in its absence.

EXAMPLE 25

In the following Example, a masterbatch having the same composition as that of Example 22 but prepared from a different lot of natural rubber, as used. Portions of the masterbatch were taken and mixed in a Banbury mixer which sulphur, 2(morpholinothio) benzothiazole and the stabiliser compound in the proportions 2.5, 0.7 and 3.0 parts by weight per 100 parts by weight of rubber. A further portion of the masterbatch to which only sulphur and 2(morpholinothio) benzothiazole were added was used as a control. The curing characteristics of the vulcanisable compositions thus obtained and the physical properties of the vulcanisates were determined as described above.

The results set out in Table 3 show improved retention of modulus and resilience on overcure.

TABLE 3

| | | | Stabiliser Compound | | | | Example No. | | | |
|---|---|---|---|---|---|---|---|---|---|---|
| | None | | 1 | | 3 | | 17 | | 18 | |
| Cure time at 141° C. (mins) | 42 | 200 | 60 | 200 | 60 | 200 | 45 | 200 | 40 | 200 |
| 300% modulus (MPa) | 16.0 | 14.2 | 16.5 | 16.6 | 16.1 | 17.1 | 15.6 | 15.6 | 17.2 | 16.4 |
| Resilience (%) | 66.7 | 58.5 | 68 | 62 | 63.6 | 62.9 | 60.5 | 58.5 | 65.0 | 58.5 |
| % retention of modulus on overcure | 88.7 | | 100.6 | | 106.2 | | 100.0 | | 95.3 | |
| % retention of resilience on | 87.7 | | 91.2 | | 98.9 | | 96.7 | | 90.0 | |

TABLE 3-continued

|  | Stabiliser Compound | | Example No. | |
|---|---|---|---|---|
| | None | 1 | 3 | 17 | 18 |
| overcure | | | | | |

EXAMPLE 26

In the following Example a masterbatch having the same composition as that of Example 22 but prepared from a different lot of natural rubber, was used. Portions of the masterbatch were taken and mixed in a Banbury mixer with sulphur and 2(morpholinothio) benzothiazole in the proportions 2.5 and 0.7 parts by weight respectively per 100 parts by weight of rubber, and with the stabiliser compound in the amounts (in parts by weight per 100 parts by weight of rubber) shown in Table 4 below. A further portion of the masterbatch to which only sulphur and 2(morpholinothio) benzothiazole were added was used as a control.

The curing characteristics of the vulcanisable compositions thus obtained and the physical properties of the vulcanisates were determined as described above.

The results set out in Table 4 below show that all the compounds exhibit modulus retention on overcure, the compound of Example 15A showing good activity at the relatively low (1.7 parts per 100 parts rubber) used. Fatigue properties are especially good with the compound of Example 15C.

Banbury mixer with sulphur, 2(morpholinothio)benzothiazole and the stabiliser compound in the proportions 2.5, 0.7 and 3.0 parts by weight respectively per 100 parts by weight of rubber. A further portion of masterbatch to which only sulphur and 2(morpholinothio)benzothiazole were added was used as a control.

The curing characteristics of the vulcanisable compositions thus obtained and the physical properties of the vulcanisates were determined as described above.

The results are given to Table 5 below. The results show that the presence of the stabiliser compound provides good retention of, or an increase in, 300% modulus on overcure. Also percentage retention of resilience on overcure is significantly higher than that of the control. Blow-out time in the Goodrich flexometer test increases during overcure on all stocks except the control, the increase being especially marked for the compounds of Examples 12, 13, 14A and 14B (cobalt, nickel, zinc and magnesium salts).

TABLE 5

| | Stabiliser Compound. Example No. | | | | | | | | | | | | | |
|---|---|---|---|---|---|---|---|---|---|---|---|---|---|---|
| | None | | 11 | | 12A | | 13 | | 14A | | 14B | | 14C | |
| Cure time at 141° C. (mins) | 40 | 200 | 40 | 200 | 60 | 200 | 60 | 200 | 60 | 200 | 60 | 200 | 60 | 200 |
| 300% Modulus (MPa) | 16.4 | 14.5 | 17.0 | 17.8 | 17.2 | 17.8 | 17.0 | 16.7 | 16.0 | 17.1 | 16.3 | 17.7 | 16.6 | 17.5 |
| Resilience (%) | 64.6 | 59.8 | 65.3 | 62.6 | 64.3 | 62.9 | 65.0 | 61.8 | 64.6 | 63.8 | 66.4 | 63.2 | 64.3 | 63.9 |
| % retention of modulus during overcure | 88.4 | | 104.7 | | 103.5 | | 98.5 | | 106.9 | | 108.6 | | 105.4 | |
| % retention of resilience during overcure | 92.6 | | 95.9 | | 97.8 | | 95.1 | | 98.8 | | 95.2 | | 99.4 | |
| Goodrich Flexometer | | | | | | | | | | | | | | |
| Heat build-up (°C.) | 21.5 | 25.5 | 21.5 | 23.0 | 23.5 | 22.0 | 20.5 | 22.5 | 23.0 | 22.0 | 24.0 | 23.5 | 20.5 | 24.0 |
| Blow-out time (mins) | 25 | 24 | 29 | 34 | 28 | >80 | 30 | 65 | 34 | 91 | 20 | 71 | 29 | 33 |

EXAMPLE 28

In the following Example a masterbatch having the same composition as that of Example 22 but prepared

TABLE 4

| | | | Stabiliser Compound. | | Example No. (Amount) | | | |
|---|---|---|---|---|---|---|---|---|
| | None | | 4 (3.0) | | 15A (1.7) | | 15C (4.0) | | 16A (3.0) | |
| Cure time at 141° C. (mins) | 40 | 200 | 60 | 200 | 40 | 200 | 60 | 200 | 40 | 200 |
| 300% modulus (MPa) | 16.9 | 15.0 | 17.2 | 16.2 | 15.4 | 16.0 | 15.6 | 16.8 | 16.9 | 17.8 |
| Resilience (%) | 63.3 | 58.5 | 65.0 | 59.8 | 63.2 | 61.5 | 62.6 | 59.8 | 63.2 | 63.6 |
| % retention of modulus on overcure | 88.8 | | 94.2 | | 103.9 | | 107.7 | | 105.3 | |
| % retention of resilience on overcure | 89.6 | | 92.0 | | 97.3 | | 95.5 | | 100.6 | |
| Goodrich flexometer | | | | | | | | | | |
| Blow out time (mins) | 22 | 21 | 18 | 38 | 23 | 33 | 24 | 31 | 29 | 35 |
| Fatigue-to-failure Kilocycles at 1 MPa strain energy | 195 | 147 | 185 | 160 | 213 | 160 | 221 | 173 | 169 | 160 |

EXAMPLE 27

In the following Example, a masterbatch having the same composition as that of Example 22 but prepared from a different lot of natural rubber, was used. Portions of the masterbatch were taken and mixed in a from a different lot of natural rubber was used. Portions of the masterbatch were taken and mixed in a Banbury mixer with sulphur, 2(morpholinothio)benzothiazole and the stabiliser compound in the proportions 2.5, 0.7 and 3.0 parts by weight per 100 parts by weight of rubber. A further portion of the masterbatch to which only sulphur and 2(morpholinothio) benzothiazole were added was used as a control.

The curing characteristics of the vulanisable compositions thus obtained and the physical properties of the vulcanisates were determined in the manner described above.

Stocks containing stabilising compounds all exhibited greater percentage retention of modulus than the control, as shown by the results set out in Table 6 below.

TABLE 6

| | Stabiliser Compound. Example No. | | | | | | | |
|---|---|---|---|---|---|---|---|---|
| | None | | 15B | | 16B | | 21 | |
| Cure time at 141° C. (mins) | 40 | 200 | 45 | 200 | 60 | 200 | 45 | 200 |
| 300% modulus | 16.1 | 14.2 | 15.7 | 16.2 | 13.9 | 14.3 | 15.3 | 15.0 |
| % retention of modulus on overcure | 88.2 | | 103.2 | | 102.9 | | 98.0 | |

The methods and materials of the invention have been shown to be useful in preparing rubber compositions of improved properties.

The compositions of the invention have been shown to be useful in the fabrication of rubber articles. Vulcanized compositions of the invention possess improved properties.

Although the invention has been illustrated by typical examples, it is not limited thereto. Changes and modifications of the examples of the invention herein chosen for purposes of disclosure can be made which do not constitute departure from the spirit and scope of the invention.

I claim:

1. A vulcanisable rubber composition comprising a diene rubber, sulphur and vulcanisation accelerator, characterised in that the composition also comprises a stabilizer material which is a compound having the formula $$MO_2S-S-X'-S-SO_3M \quad (I)$$
or
$$X[-(CH_2)_{n'}CH_2-S-SO_3M]_{n''} \quad (II)$$

where X' represents an alkylene radical or a radical comprising two or more alkylene units, pairs of such units being linked through an oxygen or sulphur atom, rhrough a group —SO$_2$—, —NH—, —NH$_2^+$—, —N(C$_{1-16}$alkyl)- or —COO—, or through an arylene or cycloalkylene radical, X is the trivalent or tetravalent analogue of X1 and in addition may contain one or more Si groups to link pairs of alkylene radicals, n' has an integral value of at least 1, n'' has the value 3 or 4, and M is a monovalent metal, the equivalent of a multivalent metal, a monovalent ion derived by the addition of a proton to a nitrogenous base, or the equivalent of a multivalent ion derived by the addition of two or more protons to a nitrogenous base.

2. A composition according to claim 1 wherein, in a stabiliser compound, each group —S—SO$_3$M is attached to a primary carbon of a bridging group.

3. A composition according to claim 1 wherein the stabiliser material is a compound having the formula I.

4. A composition according to claim 1 wherein the stabiliser material is a compound having the formula II.

5. A composition according to claim 1 wherein X represents a C$_2$ or a C$_{5-16}$ alkylene radical or a radical having the formula $$-(CH_2)_a-O-(CH_2)_a-$$

$$-(CH_2)_a-O-CH_2-O-(CH_2)_a-$$

$$-(CH_2)_b-cyclohexylene-(CH_2)_b-$$

$$-(CH_2)_c-COO-(CH_2)_a-$$

$$-(CH_2)_c-COO-Y-OOC-(CH_2)_c-$$

$$-(CH_2)_c-SO_2-(CH_2)_c- \quad \text{or}$$

$$-(CH_2)_c-NH_2^+-(CH_2)_c-$$

wherein each a independently represents an integer of from 3 to 8, b represents an integer of from 1 to 4, c represents an integer of from 3 to 12, Y represents a group —(CH$_2$)$_c$— or a group —(CH$_2$CH$_2$O)$_d$CH$_2$CH$_2$— where d represents an integer of from 1 to 5.

6. A composition according to claim 1 in which M represents an alkali metal or an equivalent of magnesium, calcium, barium, zinc, cobalt or nickel, and the stabiliser material may also contain water of crystallisation.

7. A composition according to claim 6 in which M represents sodium.

8. A composition according to claim 1 in which M represents an ammonium ion or an ion $$R^2NH_3^+, R^2R^3NH_2^+ \text{ or } R^2R^3R^4NH^+$$

where
each of R$^2$, R$^3$ and R$^4$ independently represents a C$_{1-20}$ alkyl group, a C$_{5-9}$ cycloalkyl or alkylcycloalkyl group, a benzyl group, a phenyl group or a substituted phenyl group, provided that not more than one of R$^2$, R$^3$ and R$^4$ is a phenyl or substituted phenyl group.

9. A composition according to claim 8 in which M represents an ion R$^2$R$^3$NH$^+$ where one of R$^2$ and R$^3$ is a C$_{4-12}$ tert-alkyl group and the other is a benzyl group; or where one of R$^2$ is a C$_{3-12}$ sec-alkyl group or a cyclohexyl group and the other is a 4-phenylaminophenyl group.

10. A composition according to claim 1 in which M represents a guanidinium or substituted guanidinium ion of the formula $$R^2NH-\overset{\overset{NH_2^+}{\|}}{C}-NHR^2$$

or a substituted isothiouronium ion of the formula $$\overset{+}{NH_2}=\overset{\overset{SR^5}{|}}{C}-NH_2$$

where each R$^2$ independently represents hydrogen, a C$_{1-20}$ alkyl group, a C$_{5-9}$ cycloalkyl or alkylcycloalkyl group, a benzyl group, a phenyl group or a substituted phenyl group, and R$^5$ represents a C$_{1-20}$ alkyl group, a C$_{5-9}$ cycloalkyl or alkylcycloalkyl group or a benzyl group.

11. A composition according to claim 1 in which M represents an optionally ring-substituted 1,2-dihydroquinolinium ion.

12. A composition according to claim 1 in which M represents the equivalent of a divalent ion of the formula $$R^2{}^+NH_2-A-\overset{+}{N}H_2R^2$$

where A represents a radical —(CH$_2$)$_c$— where c has a value from 2 to 20 or a phenylene radical, and each R$^2$ independently represents a C$_{1-20}$alkyl group, a C$_{5-9}$ cycloalkyl or alkylcycloalkyl group, a benzyl group or a phenyl or substituted phenyl group, provided that neither R$^2$ is phenyl or substituted phenyl when A represents phenylene.

13. A composition according to claim 12 in which A represents a para-phenylene radical and each R$^2$ represents a C$_{3-12}$ sec-alkyl group.

14. A composition according to claim 1 in which M represents the equivalent of a divalent ion of the formula

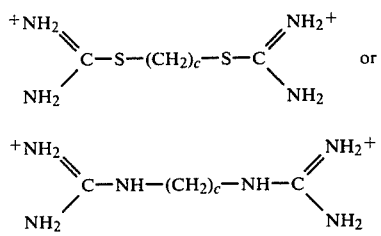

where c is an integer from 2 to 20.

15. A composition according to claim 2 wherein the stabiliser material is a compound having the formula

MO$_2$S—S—X′—S—SO$_2$OM where X′ represents a C$_{5-16}$ alkylene radical and M represents sodium or an equivalent of magnesium, calcium, barium, zinc, cobalt or nickel, which compound may also contain water of crystallisation.

16. A composition according to claim 15 wherein X′ in the formula represents a C$_{5-10}$ alkylene radical and M represents sodium or an equivalent of zinc, cobalt or nickel, and the compound may also contain water of crystallisation.

17. A composition according to claim 16 wherein the stabiliser compound is hexamethylene bis(thiosulphate) sodium salt or a hydrate thereof.

18. A composition according to claim 2 wherein the stabiliser material is a compound having the formula

MO$_2$S—S—X′—S—SO$_2$OM where X represents a C$_{5-16}$ alkylene radical and M represents an N-tertiary(C$_{4-12}$ alkyl)-N-benzylammonium ion or an N(4-phenylaminophenyl)-N-(C$_{3-12}$ sec-alkyl) ammonium ion.

19. A composition according to claim 2 wherein the stabiliser material is a compound having the formula

MOO$_2$S—S—X′—S—SO$_2$OM where X′ represents a radical

—(CH$_2$)$_c$—COO(CH$_2$)$_a$— where a represents an integer from 3 to 8, c represents an integer from 3 to 12, and M represents sodium or an equivalent of magnesium, calcium, barium, zinc, cobalt or nickel, which compound may also contain water or crystallisation.

20. A composition according to claim 19 wherein the stabiliser compound is

NaO$_3$S$_2$(CH$_2$)$_3$COO(CH$_2$)$_4$S$_2$O$_3$Na or

NaO$_3$S$_2$(CH$_2$)$_5$COO(CH$_2$)$_4$S$_2$O$_3$Na.

21. A composition according to claim 1 wherein the diene rubber is natural or synthetic cis-polyisoprene or a blend of rubbers containing at least 25% by weight of cis-polyisoprene.

22. A composition according to claim 1 in which the amount of the stabiliser compound is from 1 to 5 parts by weight per 100 parts by weight of rubber.

23. A composition according to claim 1 in which the vulcanisation accelerator is a benzothiazole-2-sulphenamide.

24. A vulcanisate that has been obtained by heating a composition according to claim 1 at vulcanisation temperature.

25. A method of preparing a rubber vulcanisate having improved physical properties, which comprises incorporating sulphur and vulcanisation accelerator into a diene rubber together with an vulcanisate-stabilising amount of a stabiliser material which is a compound having the formula $$MO_2S-S-X'-S-SO_3M \qquad (I)$$

or $$X[-(CH_2)_{n'}CH_2-S-SO_3M]_{n''} \qquad (II)$$

where X′ represents an alkylene radical or a radical comprising two or more alkylene units, pairs of such units being linked through an oxygen or sulphur atom, through a group —SO$_2$—, —NH—, —NH$_2{}^+$—, —N(C$_{1-16}$alkyl)- or —COO—, or through an arylene or cycloalkylene radical, X is the trivalent or tetravalent analogue of X′ and in addition may contain one or more Si groups to link pairs of alkylene radicals, n′ has an integral value of at least 1, n″ has the value 3 or 4, and M is a monovalent metal, the equivalent of a multivalent metal, a monovalent ion derived by the addition of a proton to a nitrogenous base, or the equivalent of a multivalent ion derived by the addition of two or more protons to a nitrogenous base, and heating the mixture thus obtained at vulcanisation temperature.

* * * * *

UNITED STATES PATENT AND TRADEMARK OFFICE
CERTIFICATE OF CORRECTION

PATENT NO. : 4,417,012
DATED : November 22, 1983
INVENTOR(S) : Philippe G. Moniotte It is certified that error appears in the above-identified patent and that said Letters Patent are hereby corrected as shown below:

Col. 25, line 51, "dired" should read --dried--.

Col. 26, line 22, "uxse" should read --use--.

Col. 28, line 46, "which" should read --with--.

Col. 31, line 44, formula "$MO_2S-S-X'-S-SO_3M$" should read --$MO_3S-S-X'-S-SO_3M$--.

Col. 31, line 51, "rhough" should read --through--.

Col. 31, line 54, "X1" should read --X'--.

Col. 32, line 1, "X" should read --X'--.

Col. 34, line 42, formula "$MO_2S-S-X'-S-SO_3M$" should read --$MO_3S-S-X'-S-SO_3M$--.

Signed and Sealed this

Twelfth Day of March 1985

[SEAL]

Attest:

DONALD J. QUIGG

Attesting Officer     Acting Commissioner of Patents and Trademarks